(12) United States Patent
Nakayama et al.

(10) Patent No.: US 8,492,145 B2
(45) Date of Patent: Jul. 23, 2013

(54) PROCESS FOR PRODUCING NERVE CELLS

(75) Inventors: Takashi Nakayama, Zushi (JP); Nobuo Inoue, Yokosuka (JP); Yasushi Kondo, Kyoto (JP); Yutaka Suzuki, Sanda (JP)

(73) Assignee: Mitsubishi Tanabe Pharma Corporation, Osaka-Shi (JP)

(*) Notice: Subject to any disclaimer, the term of this patent is extended or adjusted under 35 U.S.C. 154(b) by 539 days.

(21) Appl. No.: 10/518,749

(22) PCT Filed: Jun. 23, 2003

(86) PCT No.: PCT/JP03/07906
§ 371 (c)(1),
(2), (4) Date: Dec. 22, 2004

(87) PCT Pub. No.: WO2004/007700
PCT Pub. Date: Jan. 22, 2004

(65) Prior Publication Data
US 2005/0221479 A1    Oct. 6, 2005

(30) Foreign Application Priority Data
Jun. 24, 2002    (JP) ................. 2002-182386

(51) Int. Cl.
*C12N 5/071*    (2010.01)
*C12N 5/00*    (2006.01)
*C12N 5/02*    (2006.01)

(52) U.S. Cl.
USPC ..................... 435/368; 435/375; 435/377

(58) Field of Classification Search
USPC ......................... 435/377, 368, 375
See application file for complete search history.

(56) References Cited

U.S. PATENT DOCUMENTS 5,981,165 A * 11/1999 Weiss et al. .................. 435/4
2002/0068045 A1 * 6/2002 Reubinoff et al. ........... 424/93.7
2006/0211109 A1 * 9/2006 Totey et al. ................... 435/366

OTHER PUBLICATIONS

Arnhold et al, J Neurosurg, 93(6): 1026-1032, 2000.*
Zhang et al, Nature Biotechnology, 19: 1129-1133, 2001, IDS.*
Flax et al, Nature, 16: 1033-1039, 1998.*
Tropepe et al (Neuron, 30: 65-78, Apr. 2001).*
Suemori et al (Developmental Dynamics, 222: 273-279, 2001).*
Vitkovic et al. (AIDS Res and Human Retroviruses, 7(9): 723-727, 1991).*
Thomson et al. (Science, 282: 1145-1147, 1998).*
Itskovitz-Eldor et al (Mol Med, ;6(2): 88-95., 2000).*
Li et al (Journal of Cell Science 123: 853-860, 2009).*
Davies et al (StepAhead Australia—Traralgon, Sun Jun. 12, 2011).*
Cordero-Llana et al (Cell Death & Differentiation 18: 907-913 (May 2011)).*
Ouyang (Embryonic Stem Cell Culture in Fibrous Bed Bioreactor Dissertation, pp. 1-367, 2006).*
Kawasaki, H. et al., Proc. Natl. Acad. Sci. USA., Jan. 29, 2002, vol. 99, No. 3, pp. 1580 to 1585.
Zhang, SC. et al., Nat. Biotechnol., (2001), vol. 19, No. 12, pp. 1129 to 1133.
Reubinoff, BE. et al., Nat. Biotechnol., (2001), vol. 19, No. 12, pp. 1134 to 1140.
Kawasaki, H. et al., Neuron (2000), vol. 28, No. 1, pp. 31 to 40.
Yoshida, M et al., Experientia (1995), vol. 51, No. 2, pp. 133 to 136.
Rousselet, A. et al., Dev. Biol., (1990), vol. 137, No. 1, pp. 33 to 45.
Pataky, DM. et al., Exp. Neurol., (2000), vol. 163, No. 2, pp. 357 to 372.
Kilpatrick, TJ. et al., J. Neurosci. Res., (1993), vol. 35, No. 2, pp. 147 to 161.
Neurons and Astrocytes Influence the Development of Purified 0-2A Progenitor Cells., Glia., (1991), vol. 4, No. 6, pp. 559 to 571.
Wagner, J. et al., Nat. Biotechnol., (1999), vol. 17, No. 7, pp. 653 to 659.
Hiroshi Kawasaki et al.; Proc. Natl. Acad. Sci.; vol. 99, No. 3; Jan. 29, 2002; pp. 1580-1585.
Su-Chun Zhang et al.; Nat. Biotechnol.; vol. 19, No. 12; Dec. 2001; pp. 1129-1133.
Benjamin Reubinoff et al.; Nat. Biotechnol.; vol. 19, No. 12; Dec. 2001; pp. 1134-1140.
Hiroshi Kawasaki et al.; Neuron; vol. 28, No. 1; Oct. 2000; pp. 31-40.
M. Yoshida et al.; Experientia; vol. 51, No. 2; 1995; pp. 133-136.
Annie Rousselet et al.; Developmental Biology; vol. 137, No. 1; 1990; pp. 33-45.
David Pataky et al.; Experimental Neurology; vol. 163, No. 2; 2000; pp. 357-372.
T.J. Kilpatrick et al.; Journal of Neuroscience Research; vol. 35, No. 2; 1993; pp. 147-161.
F. Dutly et al.; Glia.; vol. 4, No. 6; 1991; pp. 559-571.
Joseph Wagner et al.; Nat. Biotechnol.; vol. 17, No. 7; 1999; pp. 653-659.
Arnhold et al., J. Neurosurg., vol. 93, pp. 1026-1032 (2000).
Nakayama, et al., Neuroscience Research, (2003), vol. 46, pp. 241-249.
Communication from the European Patent Office in connection with the corresponding European Application of Dec. 6, 2011, Application No. 03 738 499.7-2405, Applicant: Mitsubishi Tanabe Pharma Corporation.
Kondoh, Takeshi et al., "Long-Term Culture of Neutral Stem Cell Spheres: A Cytochemical and Ultrastractural Study," Biomedical Research 19(3) 209-216, 1998.

* cited by examiner

*Primary Examiner* — Gerald Leffers, Jr.
*Assistant Examiner* — Magdalene Sgagias
(74) *Attorney, Agent, or Firm* — Birch, Stewart, Kolasch & Birch, LLP

(57) ABSTRACT

To supply substantially isolated neural cells in a large amount, and to provide an application means for a neuroregenerative medicine or the like for a neurodegenerative disease, a nervous damage or the like. A method for producing a substantially isolated neural cell, comprising the step of carrying out the suspension culture of embryonic stem cells in the presence of an astrocyte conditioned medium or ingredients substantially equivalent to the conditioned medium; and a neural cell obtained thereby; a cell pharmaceutical composition comprising, as an active ingredient, the isolated neural stem cell; and a method for treating a neurodegenerative disease or nervous damage, comprising the step of introducing the neural cell into a neurodegenerative site or a nervous damage site.

8 Claims, 24 Drawing Sheets

PROCESS FOR PRODUCING NERVE CELLS

TECHNICAL FIELD

The present invention relates to a method for producing a neural cell capable of obtaining a substantially isolated neural cell, a substantially isolated neural stem cell, a substantially isolated neuron, a substantially isolated glial cell, a cell pharmaceutical composition, and a method of treating neurodegenerative disease or nervous damage.

BACKGROUND ART

Currently, mainly four methods are performed in order to prepare a neural cell from an embryonic stem cell:

① a method comprising treating a suspension culture of embryonic stem cell aggregates with retinoic acid, thereby inducing differentiation into various neural cells [Bain, G. et al, *Dev. Biol.*, 168:642-657(1995)];

② a method comprising preparing an embrioid body [referred to as EB], culturing the EB in a serum-free culture medium to obtain neural stem cells as nestin-positive cells, and culturing the neural stem cells in the presence of basic fibroblast growth factor (bFGF), to use the resulting cell in differentiation into neural cells [Okabe, S. et al., *Mech. Dev.*, 59:89-102(1996)];

③ a method comprising culturing embryonic stem cells (ES cells) on established stroma cells, to form colonies, thereby differentiating the colonies into neural cells (SDIA method) [Kawasaki H. et al., *Neuron*, 28:31-40(2000)]; and ④ a method comprising carrying out suspension culture of ES cells in the presence of leukemia inhibiting factor (LIF), to prepare neural spheres from neural stem cells existed in ES cells in an amount of about 0.2% and then differentiating the neural spheres into neural cells [Tropepe V. et al, *Neuron* 30:65-78 (2001)].

However, according to these methods, it is currently difficult to acquire sufficient amounts of cells for use in regenerative medicine from the viewpoint of teratogenicity caused by retinoic acid on differentiated cells, a time required for producing neural stem cells, the proportion of differentiation, an efficacy of yield and the like.

A neural stem cell, which is a cell having the multipotency into a neuron or a glial cell, and the self-renewal, plays a key role in transplantation regenerative medicine for the nervous system. As a method for maintaining and proliferating neural stem cells in an undifferentiated state, a neurosphere method has been established [Reynolds, B. A. et al., *J. Neurosci.*, 12:4565-4574, (1992), Reynolds, B. A. et al., *Science* 255: 1707-1710 (1992)]. According to the above-mentioned neurosphere method, when a cell population containing neural stem cells separated from the brain is cultured in DMEM: F-12 serum-free medium containing N2 supplement [insulin, transferrin, selenium and progesterone] and 20 ng/ml epidermal growth factor (referred to as EGF) and/or 20 ng/ml bFGF, only neural stem cells which can survive under the above-mentioned culture condition is proliferated. The proliferated neural stem cells are positive for a marker an intermediate filament nestin and form a cell aggregate (neurosphere), to become possible to be cultured in floating conditions. It has been found that when the above-mentioned neurosphere is cultured on a plate coated with adhesive substrate without growth factor, the cultured cells differentiate into neurons, astrocytes, oligodendrocytes or the like (multipotency). Further, it has been shown that when the neurosphere is dissociated into single cells and the resulting dissociated cells are cultured in a serum-free medium containing a growth factor, the dissociated cells form again a neurosphere (self-renewal). However, there are defects that the neurosphere is generated not from all of the cells but from a small portion of the total cell population.

In addition, as an alternative to the Neurosphere method, a monolayer culture method has been also established, wherein the method comprises culturing neural stem cells on a plate coated with an adhesive substrate, thereby proliferating and differentiating the cells. As the above-mentioned monolayer culture method, a method for performing monolayer culture comprising concentrating neural stem cells by a density gradient centrifugation [Palmer, T. D. et al., *J. Neurosci.*, 19:8487-8597(1999)], or a method comprising performing monolayer culture of neural stem cells at a low density, thereby cloning and proliferating the cells [Ray, J. et al., *Proc. Natl. Acad. Sci. USA*, 90:3602-3606 (1993), Gage, F. H. et al., *Proc. Natl. Acad. Sci. USA*, 92:11879-11883 (1995)] is performed. According to the above-mentioned monolayer culture method, since each of cells can be identified, the method is suitable for cell lineage analysis of what sort of cells neural stem cells are differentiated into. However, the method is currently not suitable for the purpose of requiring a large amount of neural stem cells, since the neural stem cells are difficult to be maintained in the undifferentiated state and the proliferation of the neural stem cells is slow.

Therefore, in either of the Neurosphere method or the monolayer culture method, it is difficult to exactly determine which cells proliferate as neural stem cells in an undifferentiated state.

DISCLOSURE OF INVENTION

An object of the present invention is to provide a method for producing neural cells, capable of attaining at least one of obtaining a substantially isolated neural cells, obtaining the neural cells in a large amount, and providing neural cells regardless of a source of embryonic stem cells. Also, an object of the present invention is to provide a substantially isolated neural stem cell which is useful as a source of cells or tissues in a neuroregenerative medicine for a neurodegenerative disease (for instance, Parkinson's disease, Alzheimer's disease or the like), spinal damage, cerebral infarction or the like. Further, an object of the present invention is to provide a neuron which is useful in regenerative medicine such as neuronal transplantation therapy for a neurodegenerative disease (for instance, Parkinson's disease, Alzheimer's disease, or the like), spinal damage, cerebral infarction or the like. Further, an object of the present invention is to provide a glial cell which is useful for transplanting at the same time with the transplantation of a neuron and a neural stem cell to direct to support differentiation and growth of a neuron, and further forming a brain-blood barrier for supplementing nutrient substances. Further, an object of the present invention is to provide a cell pharmaceutical composition which is useful in regenerative medicine such as neuronal transplantation therapy for a neurodegenerative disease (for instance, Parkinson's disease, Alzheimer's disease or the like), spinal damage, cerebral infarction or the like, capable of obtaining a stable therapeutic effect, a high therapeutic effect or the like in cell therapy. Also, an object of the present invention is to provide a method for treating a neurodegenerative disease or a nervous damage, capable of treating the state caused by a neurodegenerative disease or a nervous damage in a stable state.

Concretely, the gist of the present invention relates to:
[1] a method for producing a substantially isolated neural cells, characterized in that the method comprises carrying out the suspension culture of embryonic stem cells in the presence of an astrocyte conditioned medium or ingredients substantially equivalent to the conditioned medium;
[2] the method for producing a neural cell according to the above [1], wherein the embryonic stem cells are embryonic stem cells of a mammal;
[3] the method for producing a neural cell according to the above [2], wherein the mammal is selected from the group consisting of a mouse, a cynomolgus monkey, a human and a rat;
[4] the method for producing a neural cell according to any one of the above [1] to [3], wherein the method comprises the step (A) of carrying out the suspension culture of embryonic stem cells in the presence of an astrocyte conditioned medium or ingredients substantially equivalent to the conditioned medium, thereby forming a stem cell sphere (SCS);
[5] the method for producing a neural cell according to the above [4], comprising carrying out after the step (A), the step of:
(B) culturing the stem cell sphere (SCS) obtained in the step (A) in the presence of basic fibroblast growth factor (bFGF) and/or epidermal growth factor (EGF) and in the presence of a cell adhesion molecule, thereby obtaining a neural stem cell as a cell migrated from SCS;
[6] the method for producing a neural cell according to the above [5], wherein culture in the step (B) is carried out in the state of adhesion of the stem cell sphere (SCS) obtained in the step (A) and an adhesive culture substratum carrying a cell adhesive molecule;
[7] the method for producing a neural cell according to any one of the above [1] to [3], comprising carrying out the step of:
(A') carrying out the suspension culture of embryonic stem cells in the presence of an astrocyte conditioned medium or ingredients substantially equivalent to the conditioned medium, and in the presence of basic fibroblast growth factor (bFGF) and/or epidermal growth factor (EGF), thereby obtaining a neural stem cell in a stem cell sphere (SCS);
[8] the method for producing a neural cell according to the above [4], comprising carrying out after the step (A), the step of:
(B') culturing the stem cell sphere (SCS) obtained in the step (A) in the state of adhesion of SCS to an adhesive culture substratum carrying a cell adhesive molecule in the absence of basic fibroblast growth factor (bFGF) and/or epidermal growth factor (EGF) and in the presence of an astrocyte conditioned medium or ingredients substantially equivalent to the conditioned medium, thereby obtaining a neuron;
[9] the method for producing a neural cell according to the above [4], comprising carrying out after the step (A), the steps of:
(B) culturing the stem cell sphere (SCS) obtained in the step (A) in the presence of basic fibroblast growth factor (bFGF) and/or epidermal growth factor (EGF) and in the presence of a cell adhesive molecule; and
(C) culturing the SCS obtained in the step (B) in the state of adhesion to an adhesive culture substratum carrying a cell adhesive molecule in the absence of bFGF and/or EGF, thereby obtaining a glial cell as a cell migrated from SCS;
[10] a method for producing a neuron, comprising the step of culturing the neural stem cell obtained by the method according to any one of the above [1] to [7] in the state of adhesion to an adhesive culture substratum carrying a cell adhesive molecule in the absence of basic fibroblast growth factor (bFGF) and/or epidermal growth factor (EGF), and in the presence of an astrocyte conditioned medium or ingredients substantially equivalent to the conditioned medium;
[11] a substantially isolated neural stem cell which is differentiated from an embryonic stem cell by the method according to any one of the above [1] to [7];
[12] the neural stem cell according to the above [10], wherein the neural stem cell is cryopreserved;
[13] a substantially isolated neuron, which is obtainable by the method [8] or [10];
[14] the substantially isolated neuron according to the above [13], wherein the cell expresses at least one kind selected from the group consisting of class III β tubulin, neurofilament, tyrosinehydoxylase, glutamate decarboxylase and choline acetyltransferase;
[15] a substantially isolated glial cell, which is obtainable by the method according to the above [9];
[16] a cell pharmaceutical composition comprising, as an active ingredient, a substantially isolated neural stem cell which is differentiated from an embryonic stem cell by the method according to any one of the above [1] to [7];
[17] a cell pharmaceutical composition comprising, as an active ingredient, a substantially isolated neuron obtainable by the method according to the above [8] or [10];
[18] a cell pharmaceutical composition comprising, as an active ingredient, a substantially isolated glial cell obtainable by the method according to the above [9]; and
[19] a method for treating a neurodegenerative disease or a nervous damage, characterized in that the method comprises introducing into a neurodegenerative site or a nervous damage site at least one cell selected from the group consisting of:
(1) a substantially isolated neural stem cell which is differentiated from an embryonic stem cell by the method according to any one of the above [1] to [7];
(2) a substantially isolated neuron obtainable by the method according to the above [8] or [10]; and
(3) a substantially isolated glial cell obtainable by the method according to the above [9].

BEST MODE FOR CARRYING OUT THE INVENTION

Figure 1:
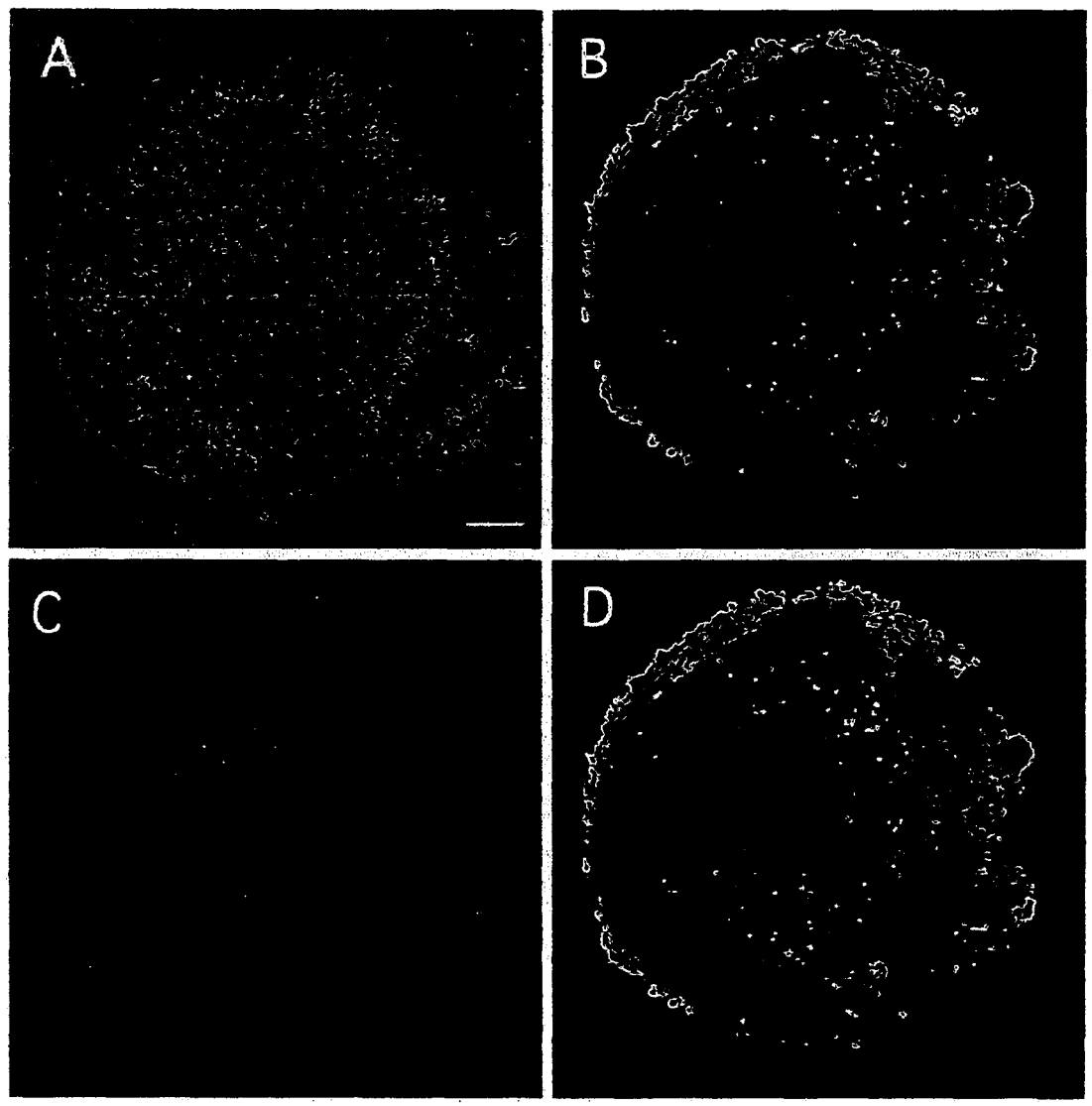
FIG. 1 is a photograph showing the results of examining the distribution of expression of nestin, which is a marker for neural stem cells, and uptake of BrdU which is used as an index of cell division, regarding colonies (SCS) of mouse embryonic stem cells (HK cell strain) obtained by carrying out the suspension culture in a mixture of an astrocyte conditioned medium and an astrocyte basal medium. A confocal laser scanning fluorescent microscope manufactured by Zeiss was used for the observation. In the figure, panel A shows a phase contrast image of SCS, panel B shows an immunofluorescent-stained image with an anti-nestin antibody, panel C shows an immunofluorescent-stained image with an anti-BrdU antibody, and panel D shows a merged image of panel B and panel C. Scale bar represents 50 μm.

One of the significant features of the method for producing a substantially isolated neural cell of the present invention resides in that the method comprises carrying out the suspension culture of embryonic stem cells in the presence of an astrocyte conditioned medium or ingredients substantially equivalent to the conditioned medium. The present invention is based on the surprising findings of the present inventors that the differentiation of the embryonic stem cells into neural stem cells can be achieved in a short period of time by carrying out the suspension culture of undifferentiated embryonic stem cells using supernatant of an astrocyte cell culture, i.e., an astrocyte conditioned medium, that the neural stem cells can be prepared in a large amount, and further that the differentiation into neurons, especially dopaminergic neurons, or glial cells especially astrocytes can be achieved by using neural stem cells that are differentiated.

According to the method for producing a neural cell of the present invention, since the astrocyte conditioned medium or ingredients substantially equivalent to the conditioned medium are used in the culture of embryonic stem cells, there is exhibited an excellent effect that a substantially isolated neural cell can be efficiently obtained from undifferentiated embryonic stem cells in a short period of time. According to the method for producing a neural cell of the present invention, a neural stem cell can be obtained in a surprisingly short period of time of, for instance, 2 to 4 days after the suspension culture of the embryonic stem cells, as compared to that of SDIA method or the like. In addition, according to the method for producing a neural cell of the present invention, since suspension culture of the embryonic stem cells is carried out, there is exhibited an excellent effect that a neural cell can be obtained surprisingly efficiently and in a surprisingly short period of time. Concretely, according to the method for producing a neural cell of the present invention, there is exhibited an excellent effect that a substantially isolated neural cell can be efficiently provided from the embryonic stem cells, without inducing ectodermal cells other than the neural cells, mesodermal cells and endodermal cells. Further, according to the method of the present invention, there is exhibited an excellent effect that embryonic stem cells can be selectively differentiated into any one kind of neurons or glial cells via the neural stem cells.

In the specification, the term "neural cell" is intended to include a neural stem cell, a nerve cell (neuron), a glial cell (for instance, an astrocyte and the like).

The above-mentioned neural stem cell refers to central nervous system undifferentiated cells having multipotency into neurons and glial cells constituting the brain, the spinal cord or the like, and having a self-renewality. The above-mentioned neural stem cell can be identified by, for instance, examining expression of a corresponding gene by a conventional method for detecting nucleic acids, or examining expression of a protein by an immunohistochemical technique, wherein expression of a marker such as nestin, RC2 or Musashi 1 is used as an index.

The above-mentioned nerve cell, i.e., neuron, is characterized by expression of a receptor for an information transmitter, for instance, expression of neurofilament, tyrosine hydroxylase, glutamate decarboxylase, choline acetyltransferase or the like. In addition, the morphological features of a neuron include cell body, dendrites, axon, axon growth cone and the like.

The nerve cell obtainable by the method for producing a neural cell of the present invention includes a neuron and the like. More concretely, the above-mentioned neuron includes a dopaminergic neuron, a GABAergic neuron, a cholinergic neuron and the like. The above-mentioned dopaminergic neuron is expected to be applied to, for instance, Parkinson's disease or the like. Also, the GABAergic neuron is a suppressive neuron and expected to be applied to suppression of hyperexcitement or the like. In addition, the cholinergic neuron is expected to be applied to Alzheimer's disease or the like.

The above-mentioned glial cell is a cell which fills a gap between a neuron and another neuron, and intermediates the metabolism of the neurons and at the same time serves as a supporting tissue. The above-mentioned glial cell includes astrocytes, oligodendrocytes and microglias for central nervous system cells. The above-mentioned glial cell includes pallial cells, Schwann cells and teloglial cells for peripheral nervous system cells. According to the method for producing a neural cell of the present invention, among the above-mentioned glial cells, especially astrocytes can be obtained. The above-mentioned astrocytes are characterized by expression of a glial fibrillary acidic protein (GFAP). Also, the morphological feature of the above-mentioned astrocytes includes numerous distinctive processes.

Concretely, the method for producing a neural cell of the present invention includes a method comprising the step of:
(A) carrying out the suspension culture of embryonic stem cells in the presence of an astrocyte conditioned medium or ingredients substantially equivalent to the conditioned medium, thereby forming a stem cell sphere (referred to as SCS).

The astrocyte conditioned medium used in the present invention is supernatant of the culture medium of astrocytes. The astrocyte conditioned medium can be obtained, for instance, by culturing astrocytes, for instance, for one day, using as a basal medium a mixed medium of Dulbecco's modified Eagle's medium (DMEM) and F-12 medium [(volume ratio=1:1 to 1:3); hereinafter the mixed medium is referred to as "DMEM: F-12"] containing, for instance, N2 supplement [insulin, transferrin, selenium, progesterone; see, for instance, Bottenstein et al., *Proc. Natl. Acad. Sci. USA*, 76: 514 (1979) or the like], and removing the astrocytes from the resulting culture, for instance, by centrifugation or the like. The basal medium for culturing astrocytes includes, for instance, DMEM, F-12, MEM, Neurobasal™ [manufactured by GIBCO BRL] and the like, in addition to the above-mentioned DMEM: F-12. These media can be prepared, for instance, on the basis of the descriptions of Frshney, R. Ian, *Culture of animal cell A manual of basic technique*, 2nd ed., Alan R. Liss. Inc., 66-84 (1987) or the like. Also, the above-mentioned astrocytes which can be used in the preparation of the astrocyte conditioned medium are not particularly limited. In addition, the astrocytes can be obtained, for instance, by removing the membrane cerebra from the brain of any animal (for instance, mouse, rat, cow, horse, pig, monkey, rabbit, or the like) such as a fetal mouse brain or a fetal rat brain, subjecting the resulting tissues to an enzyme treatment (for instance, trypsin treatment, dispase treatment or the like) which is carried out by conventional cell isolation procedures to dissociate and disperse cells, screening cells expressing a glial fibrillary producing protein, and proliferating the cells in a nutrient medium for animal cell culture [for instance, DMEM, F-12, modified Eagle's medium (MEM) or the like] containing serum from an animal such as fetal bovine serum in accordance with the previously reported method [Banker, G. et al. (eds.), *Culturing Nerve Cells*, (1991), published by The MIT Press, Cambridge, England].

The above-mentioned phrase "ingredients substantially equivalent to the conditioned medium" refers to ingredients which are capable of exhibiting the same action as that of the conditioned medium, and refers to ingredients obtained by removing the ingredients of the basal medium used and the astrocytes from the culture of astrocytes, for instance, metabolites and the like.

The embryonic stem cell used in the method for producing a neural cell of the present invention is not particularly limited in the kind of an individual to be a resource of the cell. The embryonic stem cell includes, for instance, an embryonic stem cell from, for instance, a mouse, a monkey (for instance, a cynomolgus monkey or the like), a human, a rat or the like. Concretely, the embryonic stem cell includes, for instance, HK cell strain from a mouse, 129SV cell strain from a mouse, CMK-6 cell strain from a cynomolgus monkey and the like. In the present invention, the embryonic stem cell may be a commercially available embryonic stem cell. Especially, when the neural cells obtained are used in cell transplantation therapy or the like, it is desired that the embryonic stem cell is an embryonic stem cell from an individual of the same kind as an individual to which cell transplantation therapy or the like is applied, from the viewpoint of biocompatibility.

The medium used in the culture of the embryonic stem cells includes a mixture of the astrocyte conditioned medium or ingredients substantially equivalent to the conditioned medium, with the above-mentioned astrocyte basal medium, for instance, any media such as DMEM: F-12, DMEM, F-12, MEM and Neurobasal™. It is desired that their mixing ratios are 1:1 to 1:3, as a ratio by volume.

The suspension culture of the embryonic stem cells differs depending upon the kinds of the embryonic stem cells used. For instance, it is desired that the size of a culture vessel usable in the suspension culture of the above-mentioned embryonic stem cells is a 35 mm dish, and it is desired that the concentration of the embryonic stem cells in the medium is a concentration having SCS in the number of 20 or less in a 2 ml culture medium. Further, in the case of HK cell strain, it is desired that the conditions for gas phase culture are 37° C. or so, for instance, 37°±0.2° C., a $CO_2$ concentration of 5% or so, for instance, 4.8 to 5.2%, and a humidity of 100%. Concretely, in the case of HK cell strain from a mouse or 129SV cell strain from a mouse, the suspension culture can be carried out by culturing about 10 to about 20 cells in a 35 mm dish containing 2 ml of a mixture (volume ratio=1:1) of the astrocyte conditioned medium and the astrocyte basal medium in a humidifying atmosphere of 37° C., 5% $CO_2$ in the air, and 100% humidity. It is desired that the size of the embryonic stem cells from a mouse used herein in terms of the size on feeder cell layer is a diameter of from about 400 to about 500 μm from the viewpoints of procedural facilitation, stable maintenance of the state of the embryonic stem cells, and efficient yield of the SCS. In addition, in the case of CMK-6 cell strain from a cynomolgus monkey, the suspension culture can be carried out by culturing about 10 to about 20 cells in a 35 mm dish containing 2 ml of a mixture (volume ratio=1:1) of the astrocyte conditioned medium and the astrocyte basal medium under a humidifying atmosphere of 37° C., 5% $CO_2$ in the air and 100% humidity. It is desired that the size of the embryonic stem cells from a cynomolgus monkey usable herein is a diameter of from 400 to 500 μm, from the viewpoints of procedural facilitation, stable maintenance of the state of embryonic stem cells, and efficient yield of the SCS.

Alternatively, as the above-mentioned embryonic stem cells, there can be used one that is obtained as a mass of a colony of undifferentiated stem cells by proliferating on an appropriate medium, and further on feeder cells in the state of cell adhesion, if necessary.

The SCS differs depending upon the kind of the embryonic stem cells used. In the case of the embryonic stem cells from a mouse, the SCS is formed in, for instance, 2 to 7 days, preferably 4 to 5 days under the above-mentioned conditions for the suspension culture. In the case of the embryonic stem cells from a monkey, especially a cynomolgus monkey, the SCS is formed in, for instance, 4 to 15 days, preferably 10 to 12 days under the above-mentioned conditions for the suspension culture. The formation of the SCS can be confirmed by the formation of a core structure under a stereoscopic microscope or a phase contrast inverted microscope.

Here, when the neural stem cell is produced according to the method for producing a neural cell of the present invention, from the viewpoint of efficiently obtaining of the neural stem cell, there can be preferably carried out after the step (A):
(B) culturing SCS obtained in the step (A) in the presence of bFGF and/or EGF and in the presence of a cell adhesion molecule [also referred to as "method 1 for producing a neural stem cell"].

Alternatively, there can be preferably carried out in place of the step (A):

(A') carrying out the suspension culture of embryonic stem cells in the presence of the astrocyte conditioned medium or ingredients substantially equivalent to the conditioned medium and in the presence of bFGF and/or EGF [also referred to as "method 2 for producing a neural stem cell"].

In the above-mentioned method 1 for producing a neural stem cell, the neural stem cell can be obtained as a cell migrated from SCS by carrying out the above-mentioned step (B). Also, in the above-mentioned method 2 for producing a neural stem cell, a large amount of neural stem cells can be obtained in SCS by carrying out the above-mentioned step (A').

In the above-mentioned "method 1 for producing a neural stem cell," a medium used for the culture of SCS includes a mixture of the astrocyte conditioned medium or ingredients substantially equivalent to the conditioned medium, with, for instance, Neurobasal™ B-27, DMEM: F-12, DMEM, F-12, MEM or the like, which contains bFGF and/or EGF. It is desired that the concentration of bFGF in the medium is, for instance, from 10 to 50 ng/ml, preferably from 10 to 20 ng/ml from the viewpoint of sufficiently exhibiting suppressive ability for cell differentiation and ability for cell division of the neural stem cells. In addition, it is desired that the concentration of EGF in a medium is, for instance, from 10 to 50 ng/ml, preferably from 10 to 20 ng/ml from the viewpoint of sufficiently exhibiting suppressive ability for cell differentiation. Further, when bFGF and EGF are used in combination, there may be used in admixture so as to give, for instance, a concentration of bFGF of from 10 to 20 ng/ml, and a concentration of EGF of from 10 to 20 ng/ml.

In the present invention, a substance exhibiting suppressive action on differentiation similar to the bFGF and EGF may be used in place of the bFGF and EGF mentioned above.

In the medium used in the step (B), it is desired that the mixing ratio of the above-mentioned astrocyte conditioned medium or ingredients substantially equivalent to the conditioned medium to the above-mentioned Neurobasal™ B-27, DMEM: F-12, DMEM, F-12, MEM or the like is 1:1 to 1:3 as a volume ratio.

The above-mentioned cell adhesion molecule includes polylysine, fibronectin, laminin, vitronectin, MATRIGEL™ [manufactured by BD Bioscience] and the like.

In the culture in the above-mentioned step (B), the SCS may be cultured in the state of adhesion of the SCS obtained in the step (A) to an adhesive culture substratum carrying a cell adhesion molecule, or the SCS may be cultured in a culture vessel in which a carrier carrying the cell adhesion molecule on an appropriate support is suspended or set in a three-dimensional arrangement.

The above-mentioned adhesive culture substratum includes a material in which a surface of a culturing side of the conventionally used cell culture dish is coated with the above-mentioned cell adhesion molecule or the like. For instance, when the polylysine is used as a cell adhesion molecule, an adhesive culture substratum can be obtained by sufficiently immersing the surface of a culturing side of a culture vessel (cell culture dish) in deionized water containing polylysine in a final concentration of about 0.1 mg/mg, incubating the cells at room temperature for 1 to 2 hours, and thereafter removing the solution from a culture vessel. In addition, when the fibronectin is used as a cell adhesion molecule, the cells may be incubated at 37° C. for 30 to 90 minutes using a phosphate buffered saline containing fibronectin in a final concentration of from 2 to 20 µg/ml. When the laminin is used as a cell adhesion molecule, the cells may be incubated at 37° C. for 2 hours or longer using a phosphate buffered saline containing laminin in a final concentration of from 10 to 100 µg/ml. When the vitronectin is used as a cell adhesion molecule, the cells may be incubated at 37° C. for 2 hours or longer using a phosphate buffered saline containing 1 to µg/ml vitronectin. When MATRIGEL is used as an adhesion molecule, the cells may be incubated at 37° C. for 1 hour or longer after dilution with the medium 10 to 20-folds.

Here, the adhesion of the SCS to the adhesive culture substratum can be carried out, for instance, by adding SCS to an adhesive culture substratum containing an appropriate medium.

In addition, when the above-mentioned support is suspended in a culture vessel, the support may be a support made of a substance having a smaller specific gravity than that of the medium. When the support is set in a three-dimensional arrangement in a culture vessel, the support may be a support made of the same material as that of a conventionally used cell culture dish.

The culture conditions in the above-mentioned step (B) can be appropriately set depending upon the kind of the embryonic stem cells used as a resource of the SCS to be used. For instance, it is desired that the size of the culture vessel is a 35 mm dish or a 60 mm dish. In the case of the embryonic stem cell from a mouse, it is desired that the number of colonies of embryonic stem cells, i.e., the number of SCS is, for instance, from 1 to 20, preferably from 1 to 5, more preferably from 1 to 2 in a 35 mm dish containing 2 ml of the medium. In the case of the embryonic stem cell from a monkey, it is desired that the number of colonies of embryonic stem cells is from 1 to 20, preferably from 1 to 5, more preferably from 1 to 2 in a 35 mm dish containing 2 ml of a medium. Further, in the case of those from a mouse, it is desired that the conditions for gas phase culture are 37° C. or so, for instance, 37°±0.2° C., a $CO_2$ concentration of 5% or so, for instance, 4.8 to 5.2%, and a humidity of 100%. In the case of those from a monkey, it is desired that the conditions are 37° C. or so, for instance, 37°±0.2° C., a $CO_2$ concentration of 5% or so, for instance, 4.8 to 5.2%, and a humidity of 100%.

In addition, the culture time in the above-mentioned step (B) can be appropriately set depending upon the kinds of the embryonic stem cells used. It is desired that the culture time is from 5 to 10 days in the case of the embryonic stem cells from a mouse. It is desired that the culture time is from 5 to 20 days in the case of those from a monkey.

In the above-mentioned step (B), bFGF and/or EGF may be added at an appropriate timing (for instance, in a one-day interval, a two-day interval, or the like) during the suspension culture so as to have appropriate concentrations.

According to the above-mentioned "method 1 for producing a neural stem cell," even though there are some differences depending upon the kinds of embryonic stem cells used, there are exhibited some excellent effects that in the case of the embryonic stem cells from a mouse, the SCS is formed in, for instance, 2 to 7 days after the beginning of the suspension culture under the above-mentioned conditions for the suspension culture, and the neural stem cells are obtained in a surprisingly short period of time of 2 to 5 days, preferably 2 to 4 days, and that in the case of the embryonic stem cells from a monkey, especially a cynomolgus monkey, the SCS is formed in, 4 to 15 days after the beginning of the suspension culture under the above-mentioned conditions for the suspension culture, and the neural stem cells are obtained in a surprisingly short period of time of from 4 to 7 days, preferably from 4 to 5 days.

In the step (A') of the above-mentioned "method 2 for producing neural stem cell," the medium for culturing embryonic stem cells includes a mixture of the astrocyte conditioned medium or ingredients substantially equivalent to the conditioned medium, with, for instance, Neurobasal™ B-27, DMEM: F-12, DMEM, F-12, MEM and the like, which contains bFGF and/or EGF. It is desired that the concentration of bFGF in the medium is, for instance, from 10 to 50 ng/ml, preferably from 10 to 20 ng/ml from the viewpoint of sufficiently exhibiting suppressive ability for cell differentiation and ability of cell division of the neural stem cells. In addition, it is desired that the concentration of EGF in a medium is, for instance, from 10 to 50 ng/ml, preferably from 10 to 20 ng/ml, from the viewpoint of sufficiently exhibiting suppressive ability for cell differentiation and ability of cell division of the neural stem cells. Further, when bFGF and EGF are used in combination, for instance, there may be used in admixture so as to give a concentration of bFGF of from 10 to 20 ng/ml, and a concentration of EGF of from 10 to 20 ng/ml.

In the above-mentioned "method 2 for producing neural stem cell," the suspension culture of the embryonic stem cells differs depending upon the kinds of the embryonic stem cells used. For instance, it is desired that the size of the culture vessel used in the suspension culture of the above-mentioned embryonic stem cells is a 35 mm dish as in the case of the above-mentioned step (A), that the concentration of the embryonic stem cells in the medium is 20 cells or less in 2 ml of a culture medium, and further that the conditions for gas phase culture, in the case of HK strain, are 37° C. or so, for instance, 37°±0.2° C., a $CO_2$ concentration of 5% or so, for instance, 4.8 to 5.2%, and a humidity of 100%. Concretely, in the case of the HK cell strain from a mouse or the 129SV cell strain from a mouse, the suspension culture can be carried out by culturing about 10 to about 20 cells in a 35 mm dish containing 2 ml of the medium in a humidifying atmosphere of 37° C., 5% $CO_2$ in the air and 100% humidity. In addition, in the case of CMK-6 cell strain from a cynomolgus monkey, the suspension culture can be carried out by culturing about 10 to about 20 cells in a 35 mm dish containing 2 ml of the medium in a humidifying atmosphere of 37° C., 5% $CO_2$ in the air and 100% humidity.

In addition, the culture time in the above-mentioned step (A') can be appropriately set depending upon the kinds of the embryonic stem cells used. It is desired that the culture time is from 4 to 5 days in the case of the embryonic stem cell from a mouse. It is desired that the culture time is from 7 to 10 days in the case of that from a monkey.

In the above-mentioned step (A'), bFGF and/or EGF may be added at an appropriate time (for instance, in a one day interval, a 2-day interval, or the like) during the suspension culture so as to give an appropriate concentration.

According to the above-mentioned "method 2 for producing neural stem cell," although there are some differences depending upon the kinds of the embryonic stem cells used, there are exhibited some excellent effects that in the case of the embryonic stem cells from a mouse, the SCS is formed in, for instance, 2 to 7 days under the above-mentioned conditions for the suspension culture, and the neural stem cells are obtained in a surprisingly short period of time of from 2 to 5 days, preferably from 2 to 4 days, and that in the case of the embryonic stem cells from a monkey, especially a cynomolgus monkey, the SCS is formed in, for instance, 4 to 15 days under the above-mentioned conditions of the suspension culture, and the neural stem cells are obtained in a surprisingly short period of time of from 4 to 7 days, preferably from 4 to 5 days.

Whether the cells obtained are neural stem cells can be confirmed by, for instance, examining expression of a corresponding gene by a conventional method for detecting a nucleic acid, wherein expression of a marker, for instance, nestin, RC2, Musashi 1 or the like is used as an index, or examining expression of a protein by an immunological means. Further, whether the cells obtained are neural stem cells may be confirmed by morphologies of differentiated cells or differentiated tissues generated by culturing the cells obtained in a medium which does not prevent differentiation of the cells obtained into various cells or tissues in the presence of retinoic acid or the like, or by expression of a marker specific to the differentiated cells or differentiated tissues. Moreover, the cells obtained can be confirmed by transplanting the cells obtained in the central nervous system such as forebrain, midbrain, retina, or olfactory bulb, and using the formation of neurons or the like as an index. The morphologies of the above-mentioned differentiated cells or differentiated tissues, and the marker specific to the differentiated cells or differentiated tissues include the morphological features and specific markers of the neurons and the glial cells mentioned above. The above-mentioned neural stem cells exhibit weakly positive to strongly positive property for uptake of bromodioxyuridine (BrdU) in addition to the above-mentioned index.

Here, the method for detecting a nucleic acid includes a hybridization-based detection method using a probe consisting of a nucleic acid encoding a gene to be detected or a specific fragment thereof, or a probe capable of specifically binding to the nucleic acid or a specific fragment thereof; a PCR-based detection method using a primer for amplifying a nucleic acid or a specific fragment thereof; and the like. The above-mentioned hybridization-based detection method includes, for instance, Southern hybridization, DNA array hybridization, Northern hybridization and the like. The PCR-based detection method includes, for instance, RT-PCR and the like. Here, it is desired that the nucleic acid used as a probe or a primer has a sequence of a portion specific to a nucleotide sequence of a gene to be detected. The above-mentioned "portion specific to a nucleotide sequence of a gene to be detected" can be obtained by, for instance, selecting a sequence of a portion having a sequence identity to a known sequence which is not to be detected of 20% or less, preferably 15% or less, more preferably 10% or less, further preferably 5% or less, and especially preferably 0%. The above-mentioned sequence identity can be determined by comparing two sequences which are aligned optimally over a region of sequences to be compared between two nucleic acids. Alternatively, a numerical value (percentage) of the sequence identity can be calculated by determining the identical residues which exist in both of the sequences to determine the number of matched sites, thereafter dividing the above-mentioned number of matched sites by a total number of residues existing within the region of the sequence to be compared, and multiplying the resulting numerical value by 100. For the calculations of optimal alignment and homology, for instance, local homology algorithm of Smith et al. [Add. APL. Math., 2, 482 (1981)], homology alignment algorithm of Needleman et al. [J. Mol. Biol., 48, 443 (1970)], Smith-Waterman algorithm, Good-Kanehisa algorithm, BLAST algorithm, FASTA algorithm or the like can be used. For instance, the conditions for alignment by BLAST algorithm include expect value 10, word size 3, and gap cost (Existence: 11, Extension: 1) and the like.

In addition, as the immunological technique, there can be carried out an immunological technique, for instance, conventionally used ELISA, immunostaining or the like, with an antibody or an antibody fragment against a protein to be detected or a specific fragment thereof. The antibody can be obtained by immunizing an appropriate animal, for instance, rabbit, rat, mouse, goat or the like using a marker protein to be detected in accordance with a conventional method, the method described in [for instance, *Current Protocols in Immunology*, published by John Wiley & Sons, Inc. 1992, edited by John E. Coligan, and the like].

The present invention also encompasses a substantially isolated neural stem cell which is differentiated from an embryonic stem cell according to the above method.

In addition, the neural stem cell of the present invention exhibits an excellent feature that the neural stem cell exhibits a differentiation ability into a neuron, a glial cell or the like, when the neural stem cell has been cryopreserved.

Since the neural stem cell of the present invention can be differentiated into a neuron, a glial cell or the like, there can be expected applications to neuroregenerative therapy in neurodegenerative diseases such as Parkinson's disease, Alzheimer's disease, Down's syndrome, prion disease (for instance, Creutzfeldt-Jakob disease, bovine spongiform encephalopathy and the like), polyglutamine disease (bulbar spinal amyotrophy, Huntington's disease, spinocerebellar dystonia and the like), and amyotrophic lateral sclerosis; cerebral ischemia, demyelination, head injury, spinal damage, cerebral infarct and the like.

When the neuron is prepared according to the method for producing a neural cell of the present invention, after the above-mentioned step (A), there can be preferably carried out the step of (B') culturing the SCS obtained in the step (A) in the state of adhesion of SCS to an adhesive culture substratum carrying a cell adhesion molecule in the absence of bFGF and/or EGF and in the presence of an astrocyte conditioned medium or ingredients substantially equivalent to the conditioned medium [also referred to as "method I for producing a neuron"], from the viewpoint of more efficiently obtaining the neuron. By carrying out the step (B'), the neuron can be obtained. Also, an alternative method for preparing a neuron includes a method comprising culturing the neural stem cells obtained as described above in the state of adhesion of the neural stem cells to an adhesive culture substratum carrying a cell adhesion molecule in the absence of bFGF and/or EGF, and in the presence of an astrocyte conditioned medium or ingredients substantially equivalent to the conditioned medium [also referred to as "method II for producing a neuron"].

The medium used in the above-mentioned step (B') or the above-mentioned another method includes a mixture of the above-mentioned astrocyte conditioned medium or ingredients substantially equivalent to the conditioned medium, with any media of DMEM: F-12, DMEM, F-12, MEM, Neurobasal™ and the like. It is desired that a mixing ratio is from 1:1 to 1:3 as a volume ratio. The culture conditions can be appropriately set depending upon the kinds of the embryonic stem cells used as a resource of the SCS to be used. For instance, it is desired that the size of the culture vessel is a 35 mm dish or a 60 mm dish. In the case of the embryonic stem cells from a mouse, it is desired that the number of the SCS is from 1 to 20, preferably from 1 to 5, more preferably from 1 to 2, for instance, in a culture medium containing 2 ml of a medium in a 35 mm dish. In the case of the embryonic stem cells from a monkey, it is desired that the number is from 1 to 20, preferably from 1 to 5, more preferably from 1 to 2, for instance, in 2 ml of a culture medium in a 35 mm dish. Further, in the case of those from a mouse, it is desired that the conditions for gas phase culture are 37° C. or so, for instance, 37°±0.2° C., a $CO_2$ concentration of 5% or so, for instance, 4.8 to 5.2%, a humidity of 100%. In the case of those from a monkey, it is desired that the conditions are 37° C. or so, for instance, 37°±0.2° C., a $CO_2$ concentration of 5% or so, for instance, 4.8 to 5.2%, and a humidity of 100%.

In addition, the culture time in the above-mentioned step (B') can be appropriately set depending upon the kinds of the embryonic stem cells used. In the case of the embryonic stem cells from a mouse, it is desired that the culture time is from 1 to 7 days. In the case of those from a monkey, it is desired that the culture time is from 1 to 14 days. In the case of the embryonic stem cells from a mouse, it is desired that the culture time in the method II for producing a neuron is from 1 to 7 days. In the case of those from a monkey, it is desired that the culture time is from 1 to 14 days.

According to the above-mentioned method I for producing a neuron and the above-mentioned method II for producing a neuron, there is exhibited an excellent effect that the neuron is obtained in a surprisingly short period of time of from 1 to 7 days, preferably from 2 to 5 days.

Whether the resulting cell is a neuron can be confirmed by examining expression of a corresponding gene according to the conventional method for detecting a nucleic acid using as an index expression of neurofilament, tyrosine hydroxylase, glutamate decarboxylase, choline acetyltransferase or the like, or by examining expression of a protein by an immunological technique, for instance, conventional ELISA, immunostaining or the like. Also, there can also be confirmed using as an index morphological features of a neuron such as a cell body, dendrite, axon and axon growth cone.

The present invention also encompasses a substantially isolated neuron obtained by the above method.

The neuron of the present invention is one that expresses at least one kind of selected from the group consisting of class III β tubulin, neurofilament, tyrosine hydroxylase, glutamate decarboxylase and choline acetyltransferase. There are expected applications to neuroregenerative therapy in neurodegenerative diseases such as Parkinson's disease, Alzheimer's disease, Down's syndrome, Prion disease (for instance, Creutzfeldt-Jakob disease, bovine spongiform encephalopathy or the like), polyglutamine disease (bulbar spinal amyotrophy, Huntington's disease, spinocerebellar dystonia or the like), and amyotrophic lateral sclerosis; cerebral ischemia, demyelination, head injury, spinal damage, cerebral infarct or the like.

When the glial cell is prepared according to the method for producing a neural cell of the present invention, after the step (B), there can be preferably carried out the step of (C) culturing the SCS obtained in the step (B) in the state of adhesion to an adhesive culture substratum carrying a cell adhesion molecule in the absence of bFGF and/or EGF, from the viewpoint of more efficiently obtaining a glial cell. By carrying out the step (C), a glial cell, especially an astrocyte can be obtained as a cell migrated from SCS.

The medium used in the step (C) includes Neurobasal™ B-27 [manufactured by GIBCO BRL] containing a 1 to 2% supplement, DMEM: F-12 $N_2$ supplement and the like. The culture conditions can be appropriately set depending upon the kinds of the embryonic stem cells used as a resource of the SCS to be used. For instance, it is desired that the size of a culture vessel is a 35 mm dish or a 60 mm dish. In the case of the embryonic stem cells from a mouse, it is desired that the number of SCS is from 1 to 20, preferably from 1 to 5, more preferably from 1 to 2, for instance, in 2 ml of a culture medium in a 35 mm dish, and in the case of the embryonic stem cells from a monkey, it is desired that the number is from 1 to 20, preferably from 1 to 5, more preferably from 1 to 2, for instance, in 2 ml of a culture medium in a 35 mm dish. Further, in the case of those from a mouse, it is desired that the conditions for gas phase culture are 37° C. or so, for instance, 37°±0.2° C., a $CO_2$ concentration of 5% or so, for instance, 4.8 to 5.2%, and a humidity of 100%, and in the case of those from a monkey, it is desired that the conditions are 37° C. or so, for instance, 37°±0.2° C., a $CO_2$ concentration of 5% or so, for instance, from 4.8 to 5.2%, and a humidity of 100%.

In addition, the culture time in the above-mentioned step (C) can be appropriately set depending upon the kinds of the embryonic stem cells used. In the case of the embryonic stem cells from a mouse, it is desired that the culture time is from 2 to 7 days, and in the case of those from a monkey, it is desired that the culture time is from 5 to 15 days.

According to the above-mentioned method for producing a glial cell, there is exhibited an excellent effect that a glial cell is obtained in a surprisingly short period of time of from 2 to 7 days, preferably from 5 to 7 days.

Whether the cell obtained is a glial cell, especially an astrocyte, can also be confirmed by examining expression of a corresponding gene according to the conventional method for detecting a nucleic acid using as an index expression of a glial fibrillary acidic protein (GFAP) or the like, or by examining expression of a protein by an immunological technique, for instance, the conventional ELISA, immunostaining or the like. Alternatively, there can also be confirmed using as an index morphological features of astrocytes, for instance, numerous peculiar astroidal branched dendrites.

The present invention also encompasses a substantially isolated glial cell obtained by the above method.

Since the glial cell of the present invention is an almost pure astroglial cell, there is expected an application of transplanting at the same time with transplantation of a neuron and a neural stem cell to direct to support differentiation growth of a neuron, and further forming a brain-blood barrier to supplement a nutrient substance, or the like.

The purity of the neural stem cell obtained by the method for producing a neural cell of the present invention can be obtained, for instance, as a ratio of cell-specific marker expressing cells to a total number of cells with flow cytometry using an antibody or an antibody fragment for each cell-specific marker. According to the method for producing a neural cell of the present invention, a substantially isolated neural cell is obtained.

The neural cell of the present invention can be also provided as a cell pharmaceutical composition. The cell pharmaceutical composition is also encompassed in the present invention.

Concretely, the cell pharmaceutical composition of the present invention comprises as an active ingredient a cell selected from the group consisting of the neural stem cell, the neuron and the glial cell of the present invention.

The cell pharmaceutical composition of the present invention may properly contain a pharmacological acceptable auxiliary.

In a case where a neurotransmitter, a neurotrophic factor or the like is supplied to an application site of an individual to which the cell pharmaceutical composition is to be applied, there may be used a cell pharmaceutical composition obtained by encapsulating into a capsule made of a semipermeable membrane or the like, a cell obtained by introducing a nucleic acid encoding a neurotransmitter or a nucleic acid encoding a neurotrophic factor into a neural stem cell, or a cell obtained by differentiation, if necessary, under appropriate differentiation conditions. The cell used in the cell pharmaceutical composition in which an active ingredient is encapsulated into a capsule may be a homologous cell or a heterologous cell to an individual to be applied.

In addition, according to the neural stem cells, the neurons or the glial cells of the present invention, by introducing the cells into a neurodegenerative site or a nervous damage site of an individual, the neuronal transplantation therapy can be carried out for conditions caused by diseases due to neurodegeneration or nerve damage, for instance, a neurodegenerative disease (for instance, Parkinson's disease, Alzheimer's disease or the like), and a nerve damage such as spinal damage or cerebral infarct. Therefore, a method for treating a neurodegenerative disease or a nervous damage is also encompassed in the present invention.

One of the significant features of the method for treating a neurodegenerative disease or a nervous damage of the present invention resides in that the method comprises the step of introducing at least one cell selected from the group consisting of:
(1) the neural stem cell of the present invention,
(2) the neuron of the present invention, and
(3) the glial cell of the present invention into a neurodegenerative site or a nervous damage site.

According to the treatment method of the present invention, since at least one cell selected from the group consisting of the neural stem cell, the neuron and the glial cell of the present invention is used, there are exhibited some excellent effects that a stable therapeutic effect, a high therapeutic effect or the like can be obtained in cell therapy, and that conditions caused by neurodegeneration or nervous damage can be treated in a stable condition.

The treatment method of the present invention can be applied to the diseases listed above as applications for each of the neural stem cell, the neuron and the glial cell of the present invention.

Introduction of a cell into a neurodegenerative site or a nervous damage site can be carried out by injection or the like.

In the treatment method of the present invention, there can be carried out, for instance,
  introduction of the neural stem cell of the present invention into a damage site in the case of cerebral infarct or spinal damage,
  introduction of a dopaminergic neuron, which is the neuron of the present invention, into corpus striatum or midbrain substantia nigra in the case of Parkinson's disease,
  introduction of a GABAergic neuron, which is the neuron of the present invention, into caudate nucleus in the case of Huntington's disease, and the like.

In addition, the neural stem cell, the neuron and the glial cell of the present invention can be used for the manufacture of a medicament for treating a neurodegenerative disease or a nervous damage.

The present invention will be explained more specifically hereinbelow by way of Examples, without intending to limit the present invention to these Examples. Also, in the following Examples, an astrocyte conditioned medium was used as a medium for differentiation into neural stem cells and neurons. As a basal medium for culturing astrocytes (astrocyte basal medium), DMEM: F-12 containing an N2 supplement (insulin, transferrin, selenium, or progesterone) was used. The preparation of astrocytes was carried out using a fetal mouse brain and a fetal rat brain according to a previously reported method [edited by Banker, G., *Culturing Nerve Cells* (1991), published by The MIT Press, Cambridge, United Kingdom].

EXAMPLE 1

Preparation of Neural Stem Cells

As embryonic stem cells, there was used HK cell strain (passage number: less than 10) established from C57BL/6 mouse blastocysts (3.5 days after the confirmation of vaginal plug) in accordance with a conventional method. The above-mentioned HK cells were small in the passage number, less likely to differentiate spontaneously.

Also, fibroblasts prepared from a syngenic mouse of the day 14 of pregnancy were cultured until the fibroblasts became confluent in DMEM medium containing 10% (w/v) fetal calf serum (FCS). Next, mitomycin C (1 μg/ml) was added to the cell culture obtained, and thereafter the cells were incubated for 3 hours to give inactivated cells. The inactivated cells were washed with a phosphate buffered saline, and then treated with trypsin. The cells obtained were plated on a gelatin-coated plate to give a feeder cell layer. As the above-mentioned plate, each of a 60 mm plate ($1.5 \times 10^6$ cells/plate) and a 4-well plate ($3 \times 10^5$ cells/well) was used.

The above-mentioned HK cell strain was plated on the feeder cell layer of the 60-mm plate in a concentration of 100 to 200 cells per plate. DMEM containing 15% (v/v) Knockout Serum Replacement [KSR, manufactured by GIBCO BRL], $10^3$ U/ml Leukemia Inhibitory factor [LIF, ESGRO, Chemicon International Inc., Calif., USA], 2 mM L-glutamine, 100 μM nonessential amino acids, 100 μM β-mercaptoethanol, 50 U/ml penicillin and 50 μg/ml streptomycin in a final concentration, was used as the culture medium. The medium was exchanged every 1 to 2 days.

After 7 to 10 days, a plate on which a colony of embryonic stem cells was proliferated to a size so that its diameter of about 400 to about 500 μm was washed twice or thrice with DMEM (without serum and other ingredients). The colony of embryonic stem cells was mechanically detached and picked up from the feeder cell layer with a glass capillary of which tip end was thinly worked. The obtained colony of embryonic stem cells was washed twice or thrice with DMEM without serum in a culture dish. Thereafter, the colony of embryonic stem cells was transferred to a 35 mm bacteria dish for suspension culture, of which surface on a culturing side was non-treated. Suspension culture was carried out in a mixture of the astrocyte conditioned medium and the astrocyte basal medium (ratio by volume=1:1) in a $CO_2$ incubator. The culture conditions in a $CO_2$ incubator were an atmosphere of 37° C., 5% $CO_2$ in the air, and 100% humidity. In the culture, a colony of about 10 to about 20 embryonic stem cells was cultured in 2 ml of a culture medium in a 35 mm dish. The exchange of the culture medium was not carried out during differentiation.

On the day 4 of the suspension culture, bromodeoxyuridine (BrdU) was added to the culture so as to have a final concentration of 10 μM. Uptake of BrdU is used as an index for cell division. The culture was incubated for 8 hours under the same culture conditions as above. Next, the cells obtained were cultured for 1 hour in a medium without BrdU, and washed. Thereafter, the cells obtained were immobilized with 4% (w/v) paraformaldehyde, 0.4 M sucrose, and 50 mM phosphate buffer, pH 7.4, for 30 minutes, and subjected to a treatment with 0.1% (v/v) Triton™ X-100 and blocking with 10% (w/v) BSA-PBS.

The cells after blocking (Stem Cell Sphere; hereinafter abbreviated as SCS), and an anti-nestin antibody from a mouse were incubated overnight at 4° C. The mixture obtained and a fluorescent-labeled rabbit anti-mouse IgG antibody were incubated at room temperature for 2 hours, and further incubated with a biotin-labeled mouse anti-BrdU antibody overnight at 4° C. Next, the mixture obtained and fluorescent-labeled streptoavidin were incubated at room temperature for 2 hours. Thereafter, the cells obtained were observed with a confocal laser scanning microscope (trade name: LSM510) manufactured by Zeiss. An immunofluorescent stained image is shown in FIG. 1.

As shown in FIG. 1, a strong signal for a neural stem cell marker nestin was observed (nestin-strongly positive), and a weak signal for BrdU was observed (BrdU-weakly positive) in the cell population on the SCS surface layer. Therefore, it was suggested that the group of cells of the above-mentioned SCS surface layer are neural stem cells.

In addition, a strong signal for BrdU was observed (BrdU-strongly positive) in the group of cells of a portion corresponding to a core of the SCS. Therefore, it was shown that the cell division is actively carried out in a group of cells of the portion corresponding to the core of the SCS. Further, the signal for nestin was not observed in the group of cells existing in the core of SCS. From the above results and the results of RT-PCR described later, it is thought that the group of cells of the portion corresponding to the core of SCS are undifferentiated embryonic stem cells.

In addition, a signal for either one of nestin or BrdU was not observed (nestin-negative and BrdU-negative) in the cells existing between the SCS surface layer and the core. Therefore, it was suggested that the cells existing between the above-mentioned SCS surface layer and the core are cells in the state of a transition stage in which the embryonic stem cells are differentiated into neural stem cells.

As shown in FIG. 1, it is found that the SCS formed by suspension culture using a mixture of the astrocyte conditioned medium and the astrocyte basal medium has a layered structure similar to a planet structure. Concretely, it is found that the SCS has a three-layered structure comprising a nestin-positive neural stem cell layer corresponding to the crust layer, a pre-neural stem cell layer negative to both of nestin and BrdU, the pre-neural stem cell layer corresponding to the mantle layer, and a BrdU-positive embryonic stem cell layer corresponding to the core. These structures are completely different from a structure of EB formed as an aggregate of one several embryonic stem cells according to a droplet method or the like. In the preparation of the above-mentioned EB, the embryonic stem cells are formed into an aggregate in the presence of serum, and differentiated into an endoderm, an ectoderm and a mesoderm, respectively, by indefinite various differentiation factors in serum.

By contrast, in the present Example, since the mixture of the astrocyte conditioned medium and the astrocyte basal medium used in the suspension culture of embryonic stem cells does not contain serum, it is clear that only the neural stem cells are differentiated on the SCS surface layer efficiently in a short period of time by factor(s) released from astrocytes. No aggregates could be formed when suspension culture of single embryonic stem cells dispersed from the colony was carried out in the astrocyte conditioned medium. Therefore, it is suggested that it is necessary to carry out suspension culture using a colony of undifferentiated embryonic stem cells as an aggregate, which was proliferated in a cell adhesion state for differentiation into the neural stem cells.

In addition, the size of the colony of embryonic stem cells used in the formation of the SCS was studied. As a result, in the case of a mouse, when a colony having a size of about 400 to 500 μm in a diameter was generated 7 to 9 days after single embryonic stem cells were cultured on a feeder cell layer, it was found that almost all embryonic stem cells form SCS by the same suspension culture as above. The size of the colony is equivalent to that having a diameter of about 200 to about 300 μm when the colony became spherical after the suspension culture.

EXAMPLE 2

Differentiation into Neurons

Suspension culture of the in which neural stem cells were differentiated on a surface layer [the SCS obtained in Example 1 mentioned above (4 days of suspension culture)] was carried out in a mixture of the astrocyte conditioned medium and the astrocyte basal medium (ratio by volume=1:1) in a $CO_2$ incubator in an atmosphere of 37° C., 5% $CO_2$ in the air and 100% humidity.

In order to examine the change in the differentiated states in the SCS with the passage of time, the suspension-cultured SCS was immobilized in the same manner as described above with a one- to four-day culture.

An antibody TUJ1 recognizing class III β tubulin, a marker for juvenile neurons, was used as an index of differentiation into neurons. Immunofluorescent histochemical observation was carried out by an upright fluorescent microscope (trade name: Eclipse E800) manufactured by Nikon.

As a result, cells weakly reacting with TUJ1 were observed in the inner portion of the SCS immediately after the beginning of the suspension culture.

Figure 2:
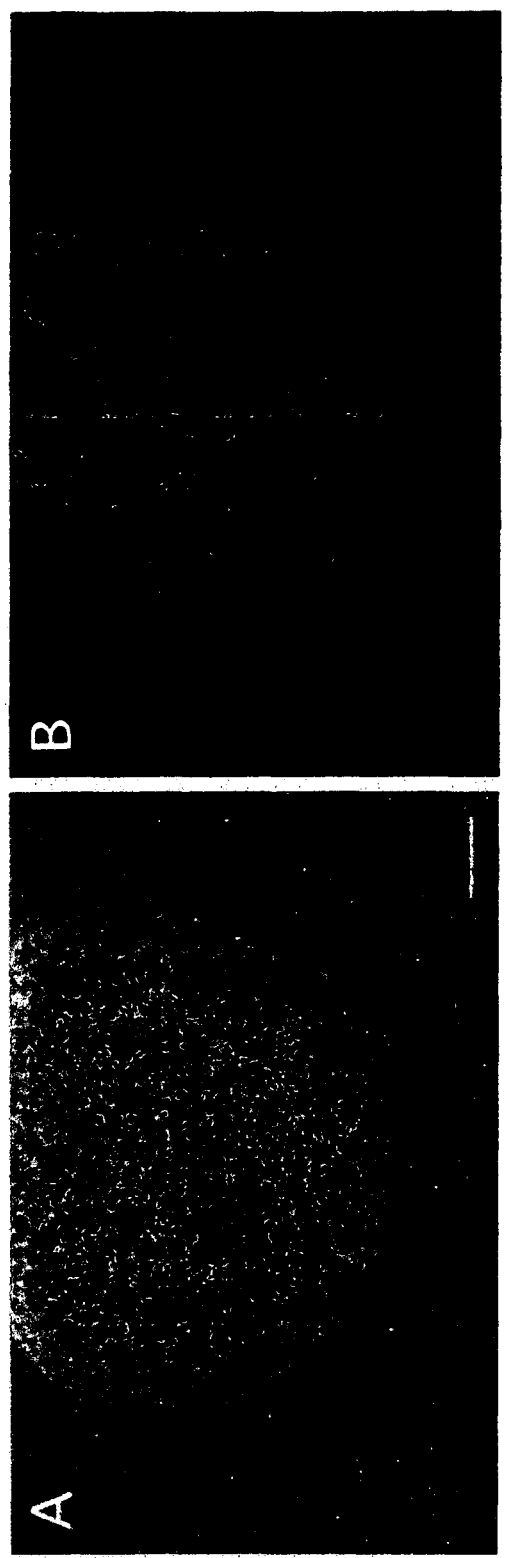
FIG. 2 is a photograph showing the results of examining expression of class III β tubulin, a marker of a juvenile neuron, in SCS in which the suspension culture is continued for 7 days. An upright fluorescent microscope manufactured by Nikon was used for the observation. In the figure, panel A shows a phase contrast image of SCS, and panel B shows an immunofluorescent-stained image with an anti-class III β tubulin antibody. Scale bar represents 50 μm.

Further, the results in which suspension culture was carried out with the above-mentioned SCS for 6 to 7 days are shown in FIG. 2.

As shown in FIG. 2, cells being strongly positive to TUJ1 and elongating a neurite lengthwise in the SCS. In other words, it is found from neurons which were differentiated in the SCS that neurites stained with an anti-class III β tubulin antibody are elongated in a network manner in the SCS. It is shown from the results that the neural stem cells can be differentiated into juvenile neurons in the state of the SCS by factor(s) in an astrocyte conditioned medium.

EXAMPLE 3

Improvement in Neuronal Differentiation Method

Neural stem cells could be prepared and differentiated into juvenile neurons by carrying out suspension culture of the SCS in a mixture of the astrocyte conditioned medium and the astrocyte basal medium.

Next, the culture optimal conditions were studied for efficiently carrying out differentiation from the neural stem cells formed on the SCS surface layer into the neurons.

The surface of a culturing side of a polylysine-coated culture dish was further treated with 0.1 mg/ml laminin or 10 to 20-fold diluted MATRIGEL™ [manufactured by BD Bioscience] to give an adhesive culture substratum. The SCS for which the suspension culture was carried out for 4 days was aspirated with a glass capillary, transferred to an adhesive culture dish to which the astrocyte conditioned medium was previously added, and the mixture was cultured in a $CO_2$ incubator for several hours in an atmosphere of 37° C., 5% $CO_2$ and 100% humidity. As a result, the SCS was adhered to the culture substratum.

Further, the morphologies of the SCS and its surroundings were observed by using a phase contrast inverted microscope [manufactured by Nikon]. As a result, there was found SCS for elongating neurites from the day 1 of the adhesion culture.

In addition, the differentiation of numerous neurons was caused by continuously carrying out adhesion culture for additional 4 to 7 days. Uptake of BrdU into cells was evaluated in the same manner as that of Example 1 mentioned above. In addition, regarding the SCS and the surroundings, expression of each of a neural stem cell marker nestin, a differentiated neuronal marker neurofilament, a dopaminergic neuron marker tyrosine hydroxylase (hereinafter abbreviated as TH), a GABAergic neuron marker glutamate decarboxylase (hereinafter abbreviated as GAD) and a cholinergic neuron marker choline acetyltransferase was examined using an antibody for each marker by an immunohistochemical technique in the same manner as the detection of nestin in Example 1 mentioned above. The results are shown in FIGS. 3 to 7.

Figure 3:
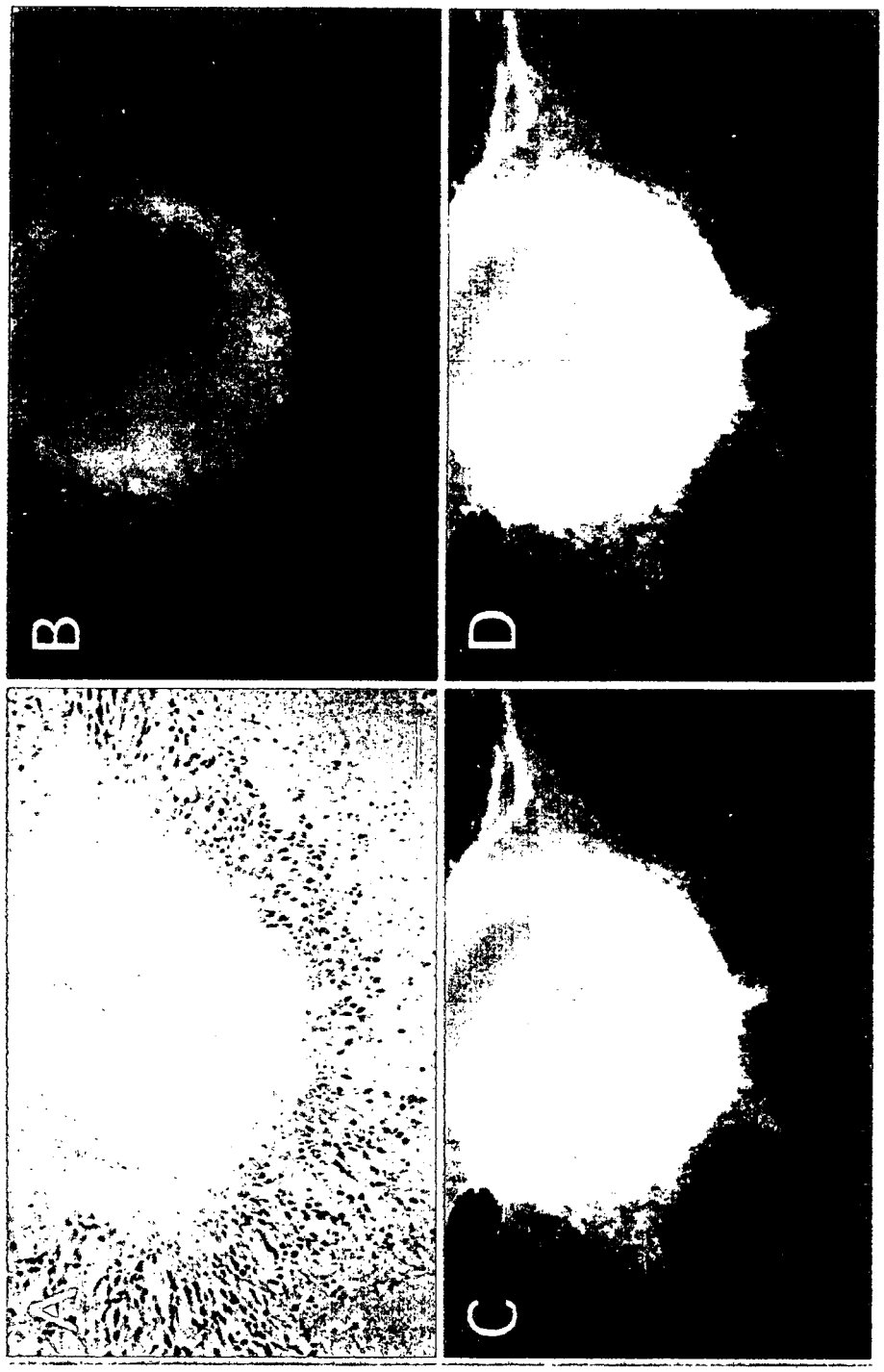
FIG. 3 is a photograph showing the results of examining differentiation into SCS which is cultured in the state of adhesion for 4 days on the surface of a culturing side (i.e. a side on which a substratum is placed therein) of a culture dish coated with an adhesive substratum on day 4 of the suspension culture. Panel A shows a phase contrast image, panel B shows an immunofluorescent-stained image with an anti-nestin antibody, panel C shows an immunofluorescent-stained image with an anti-neurofilament (NF) antibody, and panel D shows a merged image of panel B and panel C. Scale bar represents 50 μm.
Figure 4:
FIG. 4 is a photograph showing the results of examining the uptake of BrdU in SCS for which the adhesion culture was carried out, and the distribution of expression of a neurofilament. A confocal laser fluorescent microscope was used for the observation. In the figure, panel A shows an immunofluorescent-stained image with an anti-NF antibody, panel B shows an immunofluorescent-stained image with an anti-BrdU antibody, and panel C shows a merged image of panel A and panel B. Scale bar represents 50 μm.

As shown in FIGS. 3 and 4, the adhered SCSs were entirely differentiated as nestin-positive neural stem cells for uptake of BrdU and for actively carrying out the division. Further, in the surroundings of the SCS, it is found that numerous migrated neurons strongly stained with an antibody against NF, and neurites elongating from a cell body are observed, so that the nestin-positive neural stem cells exist in the inner portions thereof. In addition, as shown in FIG. 4, it is found that numerous NF-positive neurites are elongated on an adhesive culture-side. In addition, as shown in FIG. 4, it is found that a site of the in which the nestin-positive neural stem cells exist in FIG. 3 is positive to BrdU and active in the cell division.

Figure 5:
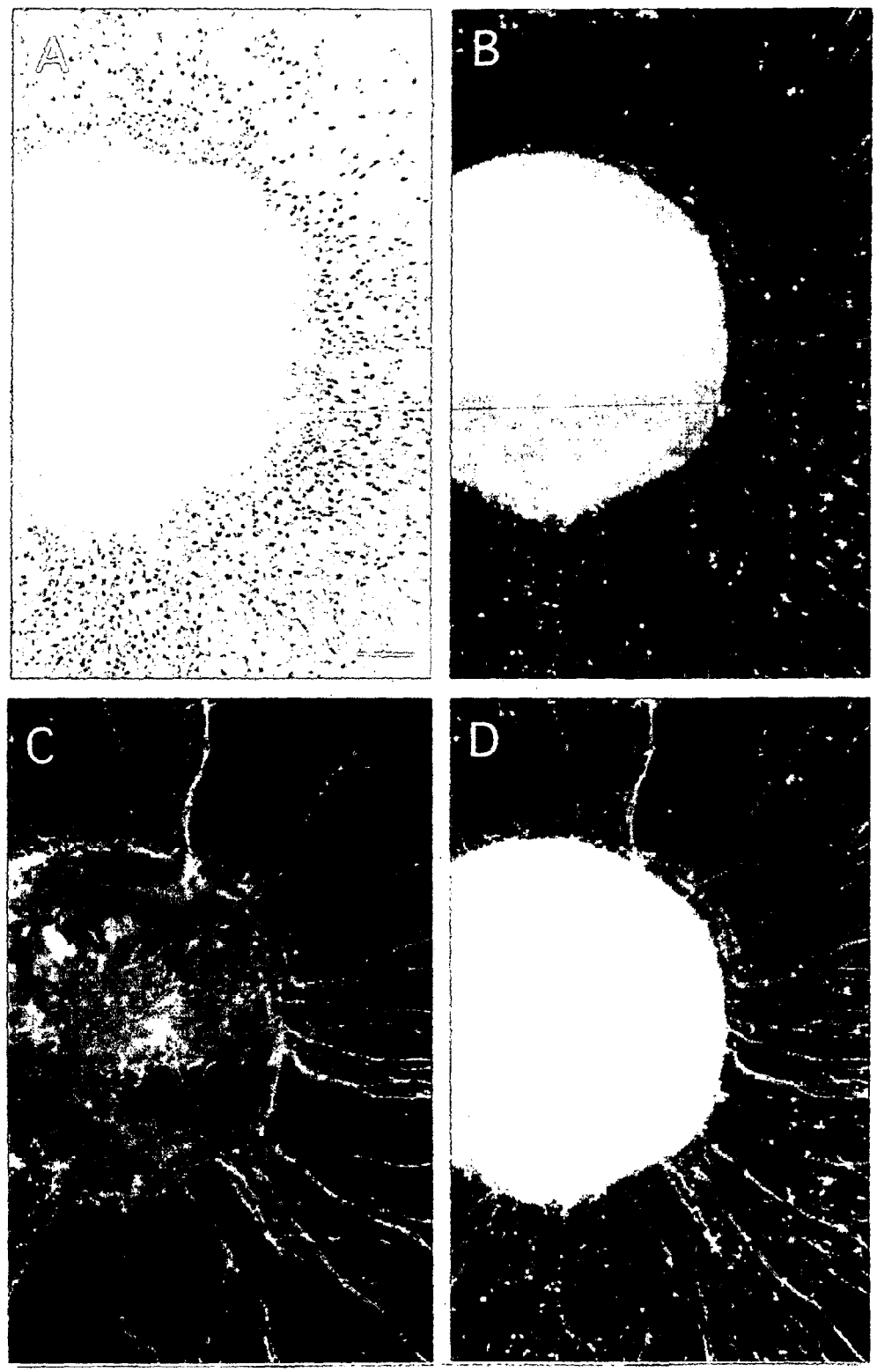
FIG. 5 is a photograph showing the results of examining expression of a neurotransmitter synthase in adhered SCS. An upright fluorescent microscope was used for the observation. In the figure, panel A shows a phase contrast image, panel B shows an immunofluorescent-stained image with an anti-NF antibody, panel C shows an immunofluorescent-stained image with an anti-tyrosine hydroxylase (TH) antibody, and panel D shows a merged image of panel B and panel C. Scale bar represents 50 μm.
Figure 6:
FIG. 6 is a photograph showing the results of examining expression of a neurotransmitter synthase in adhered SCS. An upright fluorescent microscope was used for the observation. Panel A shows an immunofluorescent-stained image with an anti-glutamate decarboxylase (GAD) antibody, panel B shows an immunofluorescent-stained image with an anti-NF antibody, and panel C shows a merged image of panel A and panel B. Scale bar represents 50 μm.
Figure 7:
FIG. 7 is a photograph showing the results of examining expression of choline acetyltransferase (ChAT). An upright fluorescent microscope was used for the observation. Panel A shows an immunofluorescent-stained image with an anti-ChAT antibody, panel B shows an immunofluorescent-stained image with an anti-NF antibody, and panel C shows a merged image of panel A and panel B. Scale bar represents 20 μm.
Figure 7:
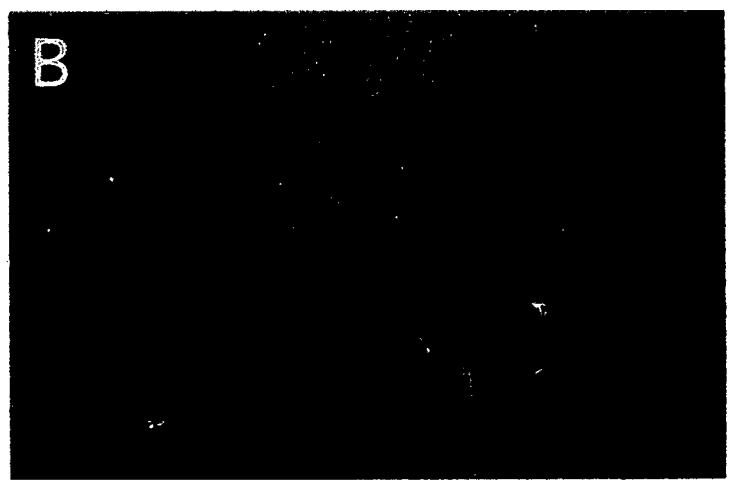
Figure 7:

Further, as shown in FIG. 5, it is found that the whole SCS is strongly stained with an antibody against a dopaminergic neuron marker TH, and that numerous elongating neurites are TH-positive. Also, as shown in FIG. 6, in the same manner as in TH, it is found that the whole SCS is strongly stained with an antibody against a GABAergic neuron marker GAD, and that numerous elongating neurites are GAD-positive. Further, as shown in FIG. 7, it is found that SCS is strongly stained with an antibody against a cholinergic neuron marker ChAT. In other words, as shown in FIGS. 5, 6 and 7, it is found that induction of expression of each of TH, GAD and ChAT takes place.

It was found that the neural stem cells on the SCS surface layer formed by suspension culture with differentiation inducing factor(s) in the astrocyte conditioned medium can be very efficiently differentiated into neurons, in cooperation with the action of the cell adhesion molecules. In addition, in a successive culture method of suspension culture and adhesion culture using the mixture of the astrocyte conditioned medium and the astrocyte basal medium, the differentiation into glial cells was not found, suggesting a possibility that inducing factor(s) secreted by astrocytes has (have) a strong action on the determination of the differentiation from neural stem cells into neurons. A ratio in which the SCS for which suspension culture was carried out in the mixture of the astrocyte conditioned medium and the astrocyte basal medium can adhere to the adhesive culture substratum was 90% or more, and a ratio of the adhered SCS for elongating neurites, an index for neuronal differentiation, was about 100%. Therefore, even if an experimental procedural error or the like is taken into consideration, it is thought that almost all of the SCSs proliferated by carrying out suspension culture using the mixture of the astrocyte conditioned medium and the astrocyte basal medium are conditioned to neural stem cells, and that the differentiation into neurons was determined by an action of cell adhesion molecules by adhesion culture. In addition, although the astrocyte conditioned medium in the adhesion culture shows an action of promoting differentiation into neurons, and the differentiation into neurons is also found in other neuronal culture medium, for instance, DMEM: F-12/N-2 supplement, Neurobasal™ B-27 [manufactured by GIBCO BRL]. It is thought that when the SCS is differentiated into neural stem cells by carrying out suspension culture, the SCS is differentiated as a default into neurons, so that exhibition of its characteristics is accelerated by an interaction with cell adhesion molecules.

It is thought that the suspension culture of the colony of embryonic stem cells is an essential condition, because the differentiation did not take place even when an aggregate of colonies of embryonic stem cells were adhered as they were and cultured in the astrocyte conditioned medium.

EXAMPLE 4

Proliferation of Neural Stem Cells

A neural stem cell layer is formed on the surface layer of the suspension-cultured SCS. When suspension culture or adhesion culture of the neural stem cells is directly carried out in the astrocyte conditioned medium, the neural stem cells are differentiated into neurons. Therefore, in order to suppress differentiation from the above-mentioned SCS into neurons and proliferate neural stem cells, the SCS after the suspension culture was cultured in an atmosphere of 37° C., a 5% $CO_2$ concentration and 100% humidity in the presence of bFGF.

The above-mentioned bFGF is a factor for maintaining the neural stem cells in an undifferentiated state and promoting cell proliferation. Therefore, the bFGF was thought to be effective also in the neural stem cells formed on the SCS surface layer. The SCS was adhered to an adhesive culture substratum in the same manner as in Example 3. Also, as the culture medium, Neurobasal™ B-27 containing 20 ng/ml bFGF as a final concentration was used. Every 1 to 2 days, the bFGF was freshly added to the culture so as to have a concentration of 20 ng/ml. The morphologies of the SCS and the surroundings were observed using an upright fluorescent microscope [manufactured by Nikon].

As a result, immediately after the adhesion culture, the differentiation into neurons was found, and elongation of neurites was observed. Cells morphologically different from those of neurons appeared and were allowed to migrate from the adhered SCS, from the days 1 to 2.

Further, uptake of BrdU into cells was examined in the same manner as that of Example 1 mentioned above. In addition, regarding the SCS and surroundings thereof, expression of a neural stem cell marker nestin, was examined using an anti-nestin antibody from a mouse by an immunohistochemical technique in the same manner as the detection of nestin in Example 1 mentioned above. The results are shown in FIG. 8.

Figure 8:
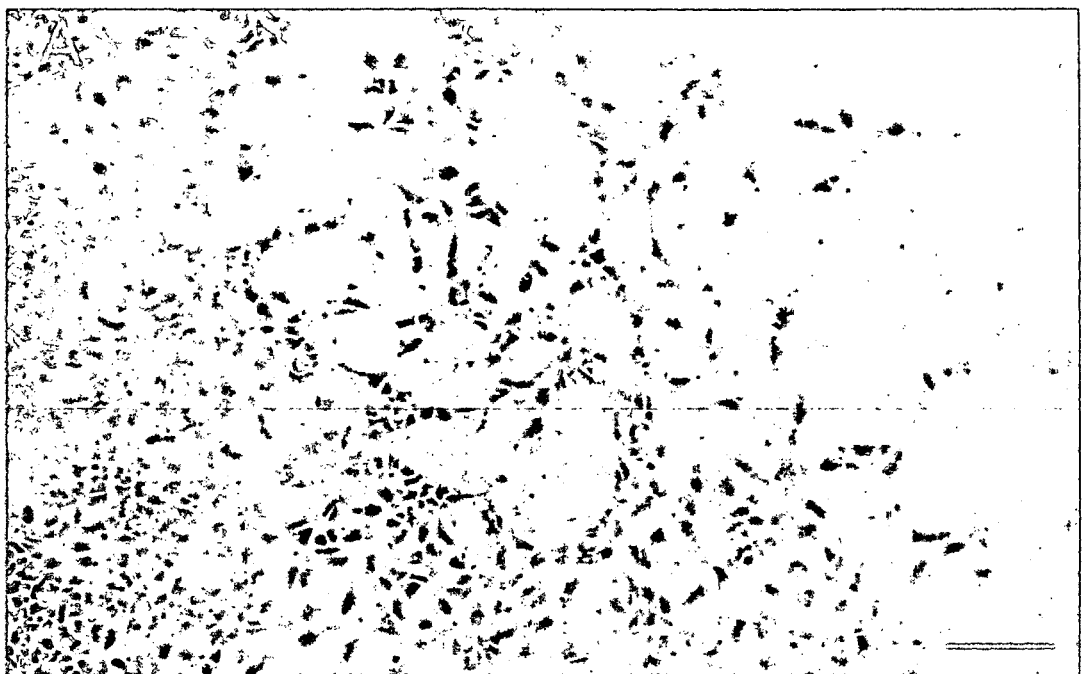
FIG. 8 is a photograph showing the results of examining SCS when the SCS was cultured in the state of adhesion, and Neurobasal™ B-27 containing bFGF was used as a culture medium. Panel A shows a phase contrast image, and panel B shows an immunofluorescent-stained image with an anti-nestin antibody. Scale bar represents 50 μm.
Figure 8:
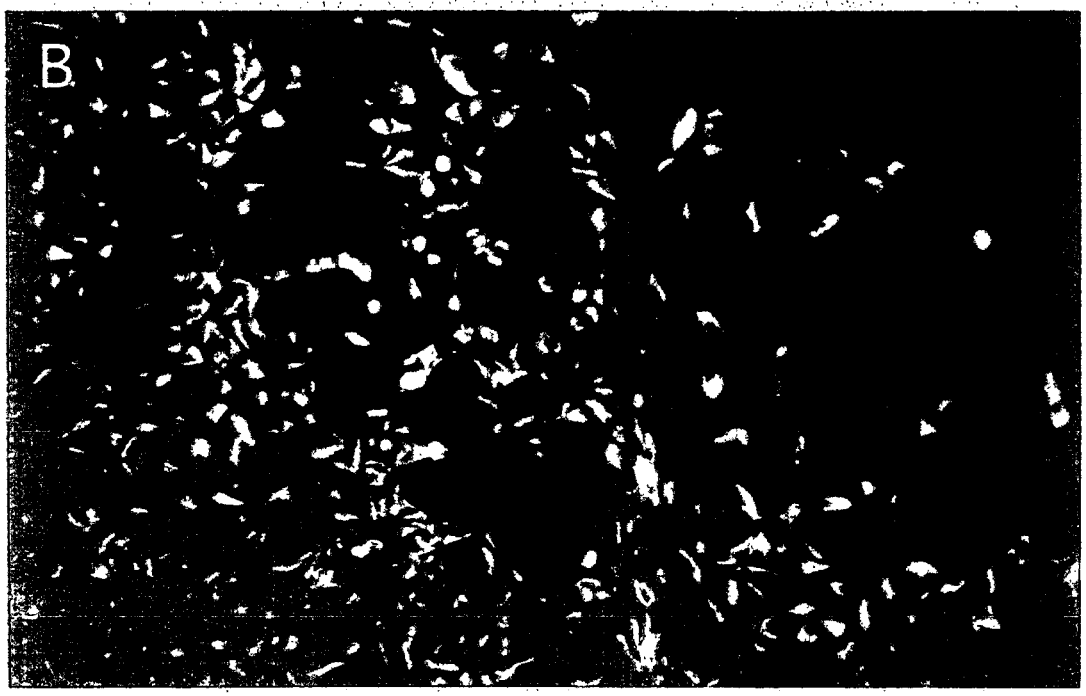

As shown by the results of immunofluorescent histochemistry in FIG. 8, it is found that migrating cells which are nestin-positive are neural stem cells. In other words, it is found that the differentiation into neurons is suppressed and that nestin-positive neural stem cells are proliferated, so that numerous cells are allowed to migrate from SCS, by exchanging a culture medium of the mixture of the astrocyte conditioned medium and the astrocyte basal medium with Neurobasal™ B-27 containing bFGF.

Figure 9:
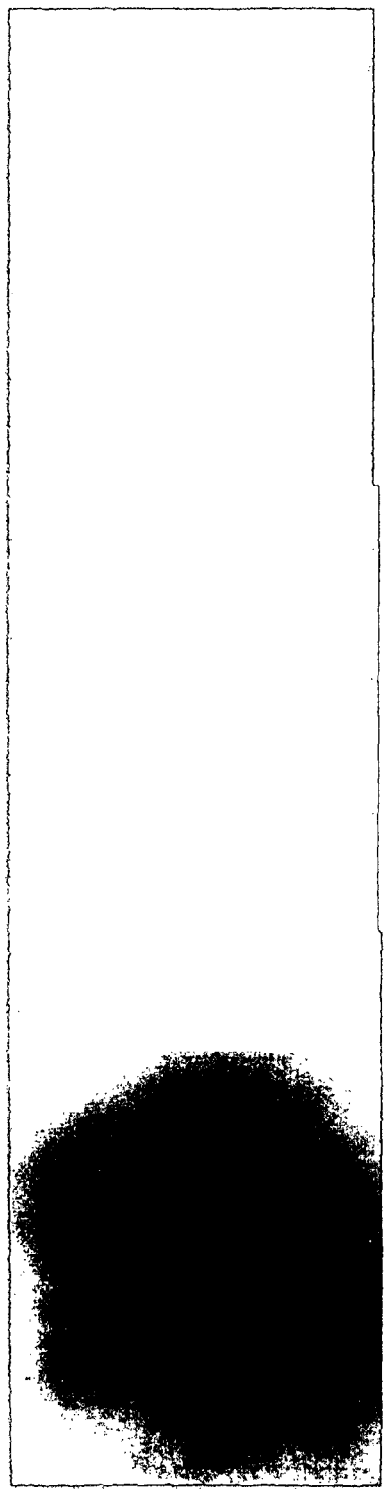
FIG. 9 is a photograph showing a colony of neural stem cells migrated from one SCS. Scale bar represents 50 μm.

In addition, the results of observation of the colony of neural stem cells which was spread from one SCS are shown in FIG. 9. As a result, as shown in FIG. 9, it is found that numerous neural stem cells are obtained surprisingly homogeneously. It is found that migrating neural stem cells which are closely adhered to each other, and allowed to migrate concentrically in a radius of about 600 µm centering about the SCS adhered to the culture substratum, so that a large amount of the neural stem cells are obtained from a single SCS. In Neurosphere method and other monolayer culture methods, since it is difficult to prepare homogeneously numerous neural stem cells as described above, it is found that the method in the present example is excellent.

In addition, as in the present example, the method for producing neural stem cells using the SCS has an excellent feature that the SCS can be used as a seed of a colony of migrating neural stem cells a number of times. In other words, after the SCS is adhered to allow the neural stem cells to migrate from the SCS, the neural stem cells can be migrated again by picking up the SCS at the center with a glass capillary and transferring the SCS to a fresh adhesive culture substratum.

Figure 10:
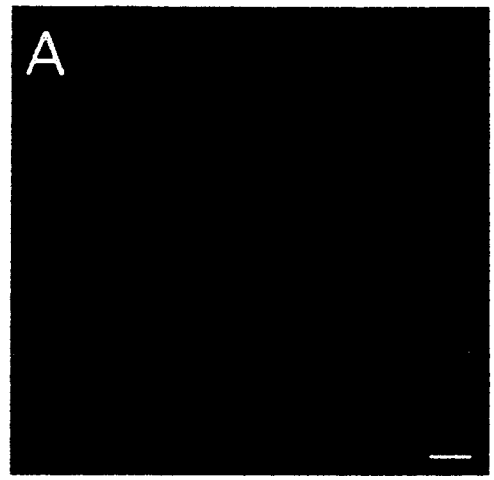
FIG. 10 is a photograph showing the results of examining the uptake of BrdU and the distribution of expression of nestin in SCS for allowing the neural stem cells to migrate in Neurobasal™ B-27 containing bFGF. Panel A shows an immunofluorescent-stained image with anti-BrdU, panel B shows an immunofluorescent-stained image with an anti-nestin antibody, and panel C shows a merged image of panel A and panel B. Scale bar represents 50 μm.
Figure 10:
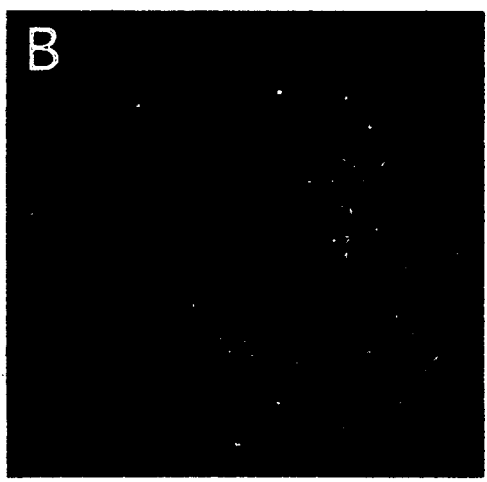
Figure 10:
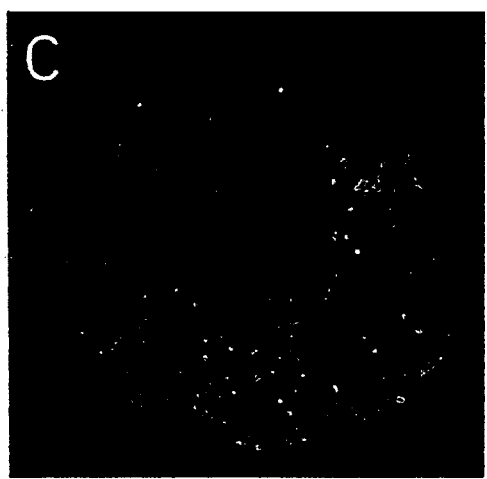

Distribution of uptake of BrdU and expression of nestin in the SCS which allows the neural stem cells to migrate in Neurobasal™ B-27 containing bFGF was examined. The results are shown in FIG. 10. As shown in FIG. 10, it is found that the SCS which is adhered and allows neural stem cells to migrate is BrdU-positive, so that staining with an anti-BrdU antibody is intensive at a core portion of the SCS, but uptake of BrdU is spread in the entire SCS as compared to that of FIG. 1. In addition, as shown in FIG. 10, since a part other than a core is stained with an anti-nestin antibody, it is found that a ratio of differentiated neural stem cells in the inner portion of the SCS is increased. It is thought that the migration to a culture substratum occurred due to proliferation of the neural stem cells in the SCS. Since the itself is actively repeating cell divisions as neural stem cells, the SCS can be used as a seed a number of times.

According to the present example, it is shown that numerous neural stem cells can be prepared by adhesion culture of the SCS in the presence of bFGF.

EXAMPLE 5

When the SCS was formed by carrying out suspension culture of a colony of HK cells of mouse embryonic stem cells in the mixture of the astrocyte conditioned medium and the astrocyte basal medium, from the beginning of the suspension culture of the HK cells, suspension culture was carried out in a medium containing 20 ng/ml bFGF as a final concentration [the mixture (ratio by volume=1:1) of the astrocyte conditioned medium and the astrocyte basal medium] in a $CO_2$ incubator. The culture conditions in a $CO_2$ incubator were an atmosphere of 37° C., 5% $CO_2$ in the air and 100% humidity. In the culture, a colony of about 10 to about 20 embryonic stem cells was cultured in 2 ml of a culture medium in a 35 mm dish. Every 1 to 2 days, the bFGF was added to a culture during the suspension culture so as to have a final concentration of 20 ng/ml.

In the day 4 of the suspension culture, bromodeoxyuridine (BrdU) was added to a culture so as to have a final concentration of 10 µM. Uptake of BrdU is used as an index for cell division. The culture was incubated for 8 hours under the same culture conditions as those mentioned above. Next, the cells obtained were cultured for 1 hour in a medium without BrdU, and washed. Thereafter, the resulting cells were immobilized with 4% (w/v) paraformaldehyde, 0.4 M sucrose and 50 mM phosphate buffer, pH 7.4, for 30 minutes, and subjected to a treatment with 0.1% (v/v) Triton™ X-100 and to blocking with 10% (w/v) BSA-PBS.

The cells (Stem Cell Sphere; hereinafter abbreviated as SCS) after blocking and an anti-nestin antibody from a mouse were incubated overnight at 4° C. The mixture obtained and a fluorescent-labeled rabbit anti-mouse IgG antibody were incubated at room temperature for 2 hours, and further incubated with a biotin-labeled mouse anti-BrdU antibody overnight at 4° C. Next, the mixture obtained and the fluorescent-labeled streptoavidin were incubated at room temperature for 2 hours. Thereafter, the cells obtained were observed with a confocal laser scanning microscope manufactured by Zeiss (trade name: LSM510). Immunofluorescent stained images are shown in FIG. 11 in which the distribution of nestin, which is a marker for neural stem cells, and BrdU, which is used as an index for cell divisions, was examined.

Figure 11:
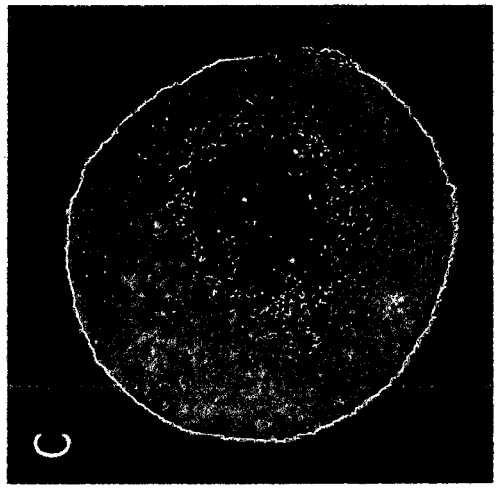
FIG. 11 is a photograph showing the results of examining the distribution of nestin, which is a marker for neural stem cells, and BrdU, which is used as an index of cell division, when bFGF is added to a suspension culture medium from the beginning of the preparation of SCS from HK cell strain of mouse embryonic stem cells. In the figure, panel A shows an immunofluorescent-stained image with an anti-nestin antibody. In the figure, panel B shows an immunofluorescent-stained image of an anti-BrdU antibody. Panel C shows a merged image of panel A and panel B. Scale bar represents 50 μm.
Figure 11:
Figure 11:
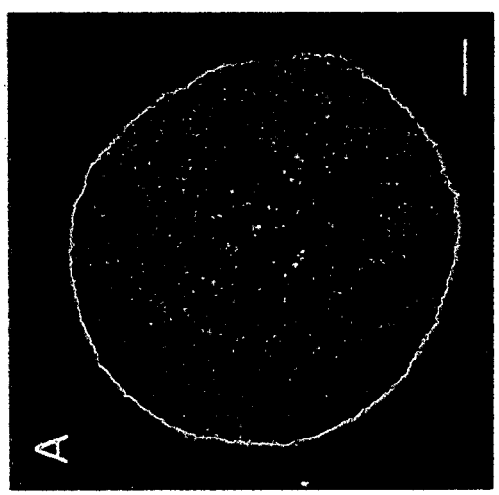

As shown in FIG. 11, a majority of the SCS surface layer except for the core became nestin-positive cells, and were proliferating. These cells were also BrdU-positive. It was shown that the neural stem cells can be prepared surprisingly efficiently by the addition of a neural stem cell growth factor bFGF, to the mixture of the astrocyte conditioned medium and the astrocyte basal medium.

EXAMPLE 6

Differentiation of Proliferated Neural Stem Cells to Neurons

Whether or not the neural stem cells obtained in Example 4 are differentiated into neurons in the same manner as in the neural stem cells formed on the SCS surface layer was examined. Concretely, whether or not the neural stem cells can be differentiated into neurons was examined by culturing the SCS in Neurobasal™ B-27 containing bFGF to give migrating neural stem cells, and exchanging the culture medium for the above-mentioned neural stem cells of which differentiation was suppressed, with the mixture of the astrocyte conditioned medium and the astrocyte basal medium in an atmosphere of 37° C. or so, a $CO_2$ concentration of 5% or so, and 100% humidity. The results are shown in FIG. 12.

Figure 12:
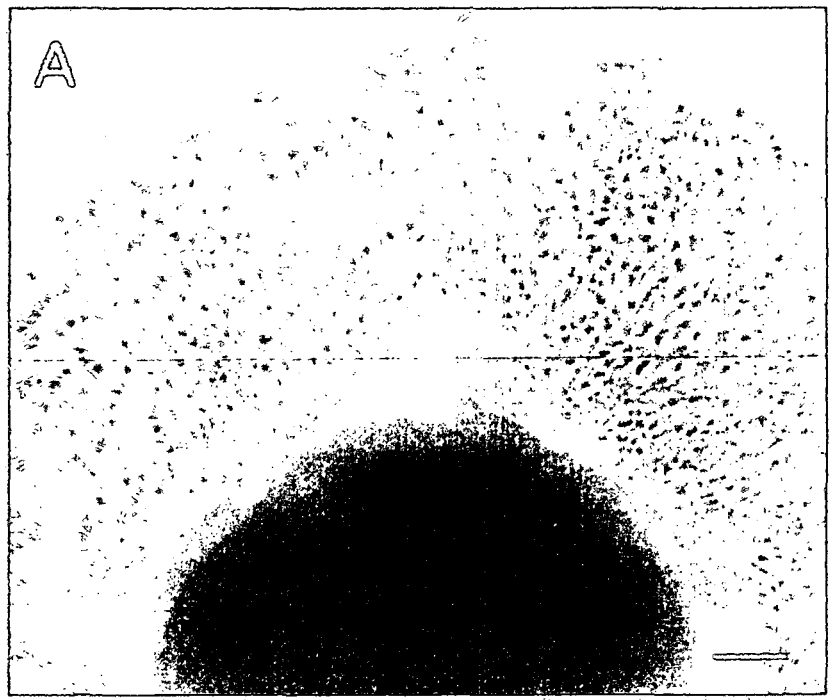
FIG. 12 is a photograph showing the results of examining the distribution of neural stem cells migrated from SCS, in neurons. In the figure, panel A shows a phase contrast image of SCS and neural stem cells immediately after Neurobasal™ B-27 containing bFGF was exchanged with a mixture of an astrocyte conditioned medium and an astrocyte basal medium, and panel B shows a phase contrast image one day after the exchange. Scale bar represents 50 μm.
Figure 12:

As shown in FIG. 12, it is found that regarding the neural stem cells in which the cells had been closely adhered to each other, by exchanging the medium with the mixture of the astrocyte conditioned medium and the astrocyte basal medium, the migrated neural stem cells are dispersed and spread while the cells are closely adhered to each other one day later to differentiate in their morphologies into neurons. In addition, it is found that the migrated neural stem cells are also differentiated into neurons by the astrocyte conditioned medium in the same manner in the neural stem cells formed on the SCS surface layer. The results suggest that the production of a large amount of neurons can be accomplished directly from the neural stem cells which were produced in a large amount.

Figure 14:
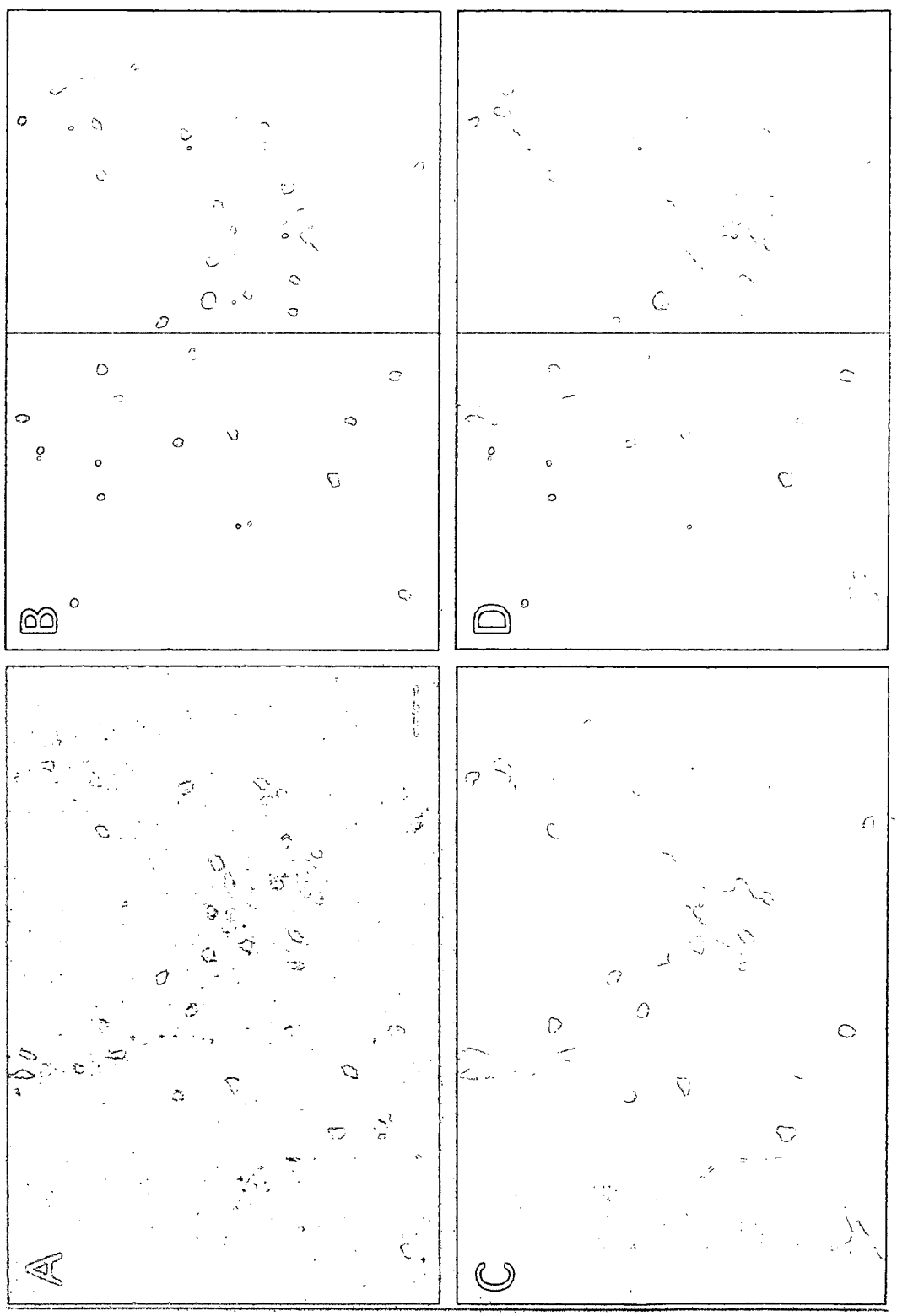
FIG. 14 is a photograph showing the results of examining the distribution of expression of TH and GAD in neurons from migrated neural stem cells. In the figure, panel A shows a phase contrast image, panel B shows an immunofluorescent-stained image with an anti-TH antibody, panel C shows an immunofluorescent-stained image with an anti-GAD antibody, and panel D shows a merged image of panel B and panel C. Scale bar represents 20 μm.
Figure 15:
FIG. 15 is a photograph showing the results of examining the presence of serotonin of a neurotransmitter in neurons from migrated neural stem cells. In the figure, panel A shows a phase contrast image, and panel B shows an immunofluorescent-stained image with an anti-serotonin antibody. Scale bar represents 20 μm.
Figure 15:
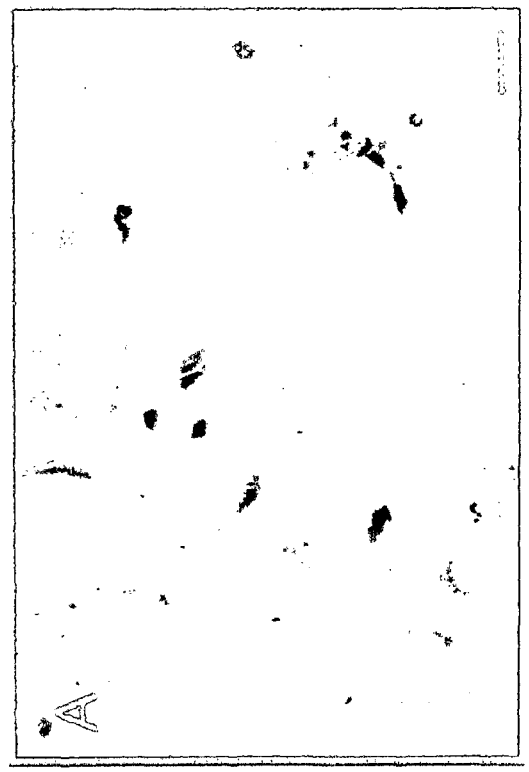

In addition, uptake of BrdU into cells was examined in the same manner as in Example 1 mentioned above. In addition, regarding the SCS and its surroundings, expression of each of a neural stem cell marker nestin, a differentiated neuron marker neurofilament, a dopaminergic neuron marker tyrosine hydroxylase (hereinafter abbreviated as TH), a GABAergic neuron marker glutamate decarboxylase (hereinafter abbreviated as GAD), and a cholinergic neuron marker choline acetyltransferase was examined using an antibody for each marker by an immunohistochemical technique in the same manner as the detection of nestin in Example 1 mentioned above. The results are shown in FIGS. 13, 14 and 15.

Figure 13:
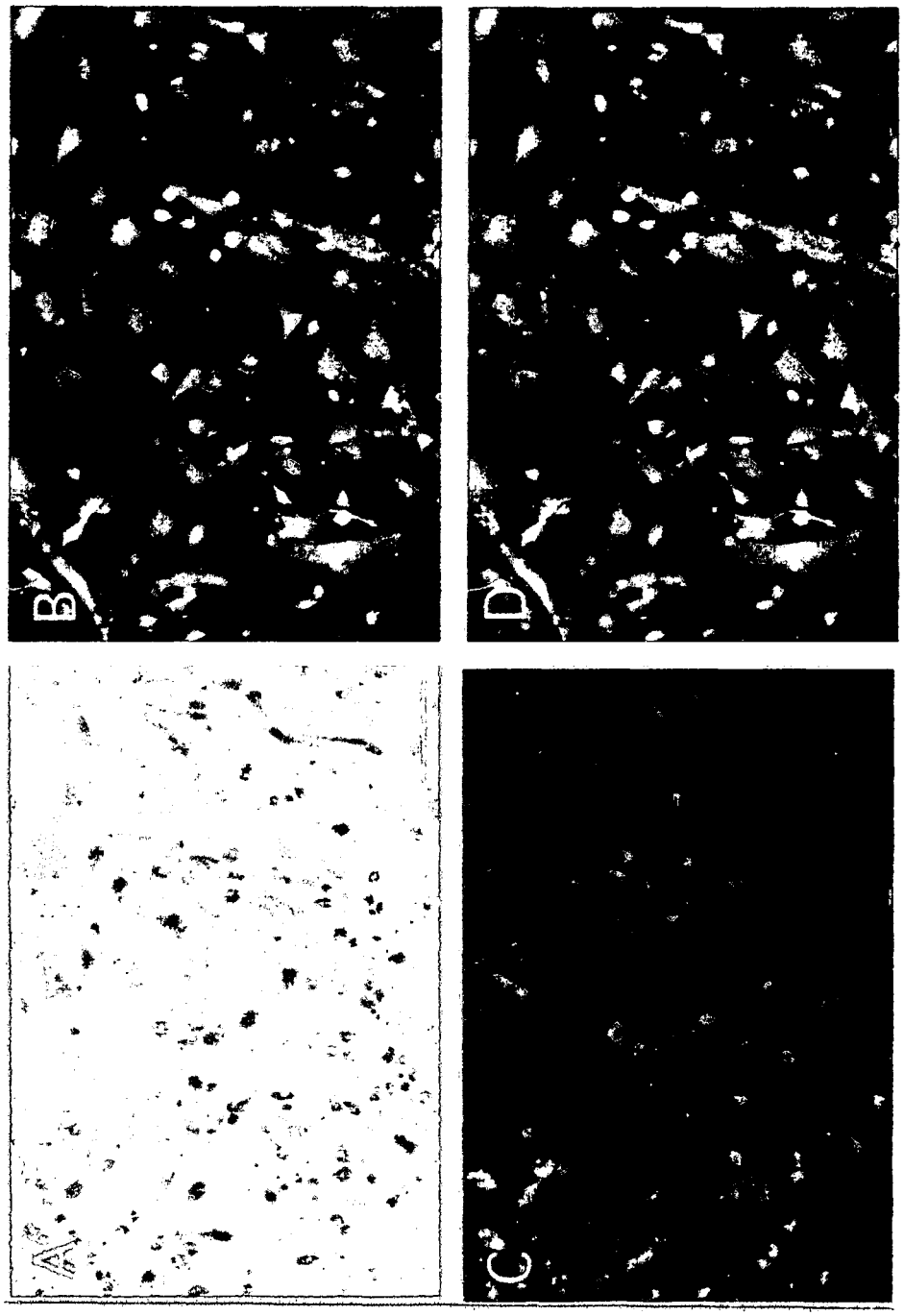
FIG. 13 is a photograph showing the results of examining expression of a neurotransmitter synthase in neurons from migrated neural stem cells. In the figure, panel A shows a phase contrast image, panel B shows an immunofluorescent-stained image with an anti-NF antibody, panel C shows an immunofluorescent-stained image with an anti-TH antibody, and panel D shows a merged image of panel B and panel C. Scale bar represents 20 μm.

As shown in FIG. 13, it is found that a dopaminergic neuron marker TH is expressed in a majority of NF-positive neurons. In other words, it is found that TH-positive neurons are differentiated not only from neural stem cells remaining in the inner portion of the SCS but also from the migrated neural stem cells. In addition, as shown in FIG. 13, neurons showing coexpression of TH and GAD were found in neurons from migrated neural stem cells, suggesting the presence of immature neurons. Further, as shown in FIG. 15, there could be confirmed neurons containing a neurotransmitter serotonin in the cells. It is found from these results that there are exhibited excellent effects by using proliferated neural stem cells:

① that homogeneous neurons which could not be prepared by a conventional, previously reported method can be prepared in a large amount, ② that neurons necessary for High Throughput Screening can be provided, because actively dividing embryonic stem cells are used as a starting material, and ③ that engineered neurons, which had been difficult to be prepared when primary cultured neurons prepared from the brain were used, can be also prepared in a large amount.

EXAMPLE 7

Differentiation of Proliferated Neural Stem Cells into Astrocytes

Since the neural stem cells are multipotent cells, whether the cells can be differentiated into cell species other than neurons was studied by changing the culture conditions.

At a time point where the SCS was cultured in the same manner as in Example 4 to allow the neural stem cells to migrate from adhered SCS, thereby forming a spread colony, Neurobasal™ B-27 containing bFGF was exchanged with Neurobasal™ B-27 without bFGF, and the culture was continued in an atmosphere of 37° C. or so, a $CO_2$ concentration of 5% or so, and 100% humidity.

As a result, in the same manner as in the differentiation into the neurons, cells which had been in a state of adhesion to each other in the surroundings of the colony were individually dissociated several days after. Further, the dissociated cells were differentiated into cells having numerous branched projections, distinctively owned by astrocytes. At this stage, expression of a glial fibrillary acidic protein (GFAP), which is a marker for astrocytes, was examined by immunofluorescent histochemistry.

Figure 16:
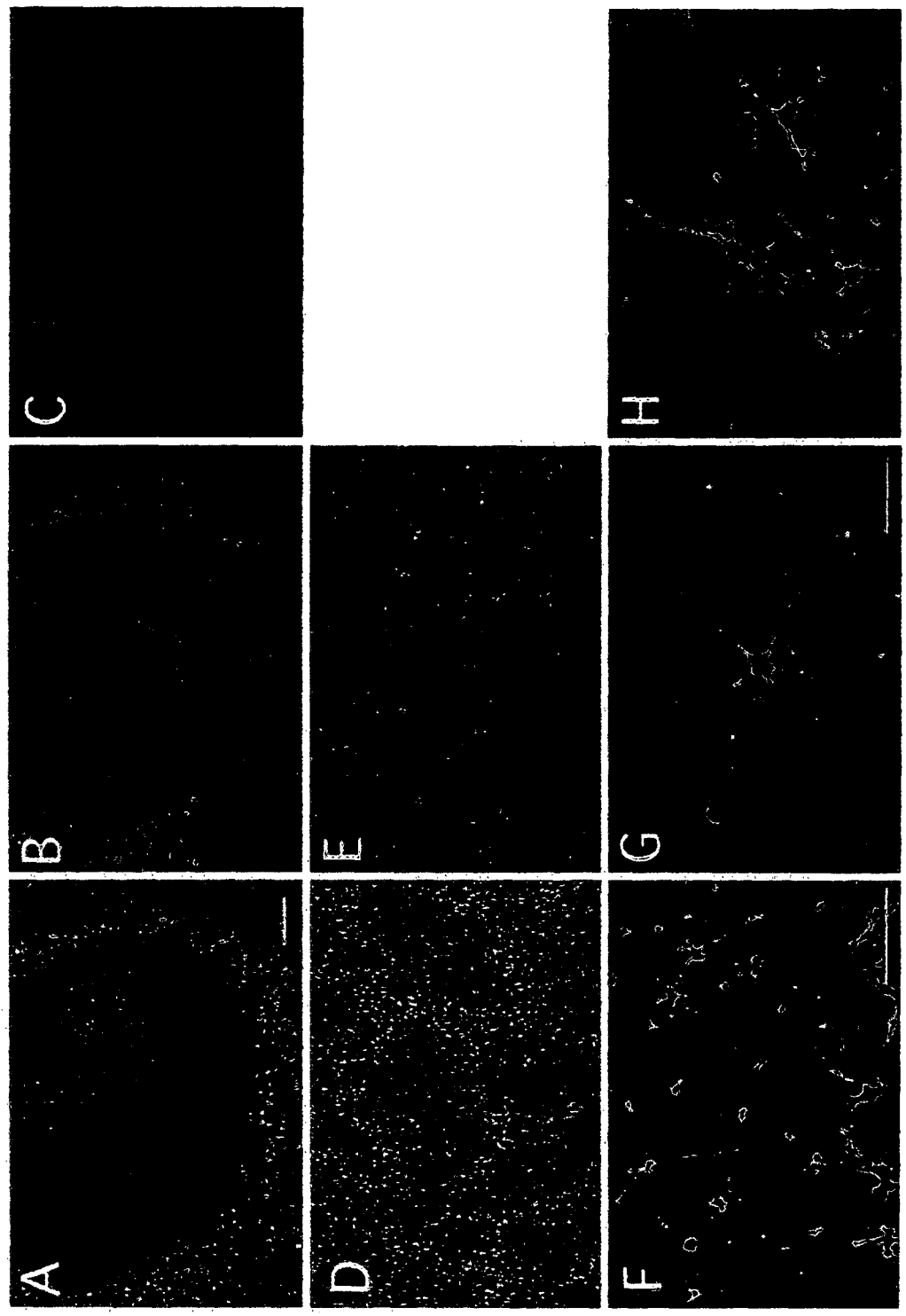
FIG. 16 is a photograph showing the results of examining the differentiation from migrated neural stem cells into astrocytes. In the figure, panel A shows a phase contrast image centering about SCS, panel B shows an immunofluorescent-stained image with an anti-GFAP antibody at the same site as that of panel A, panel C shows a stained image of the control with an anti-NF antibody at the same site as that of panel A, panel D shows a phase contrast image at a site away from SCS, panel E shows an immunofluorescent-stained image with an anti-GFAP antibody at the same site as that of panel D, panel F shows an immunofluorescent-stained image with an anti-GFAP antibody in the surrounding portions of a colony, panel G similarly shows an immunofluorescent-stained image (high magnification) with an anti-GFAP antibody in the surrounding portions of a colony, and panel H shows an immunofluorescent-stained image (high magnification) with an anti-GFAP antibody in the surrounding portions of a colony. Scale bars of panels A to F represent 50 μm, and scale bars of panels G and H represent 20 μm.

As a result, as shown in FIG. 16, it is found that all of SCSs as seeds by which neural stem cells were continued to be supplying and migrated neural stem cells are differentiated into GFAP-positive astrocytes, that are NF-negative. In addition, as shown in FIG. 16, in the surrounding portions of the colony, short branched projections distinctively owned by astrocytes was stained with an anti-GFAP antibody. In other words, it is found together with Example 6 that the neural stem cells can be determined to be differentiated into either neurons or astrocytes by changing the culture conditions.

In other words, it had been conventionally difficult to differentiate restrictively neural stem cells into one cell species. However, according to the method of the present example, since substantially homogeneous neural stem cells can be prepared in a large amount, the neural stem cells can be restrictively differentiated into one cell species. Therefore, the method using the SCS as in the present example can be expected to have effectiveness for teratogenesis, canceration or the like of transplanted cells, which is the most serious problem in regenerative therapy, transplantation therapy or the like.

EXAMPLE 8

Differentiation of Dispersed Neural Stem Cells into Neurons

Figure 17:
FIG. 17 is a photograph showing the results of examining the differentiation of dispersed migrating neural stem cells into neurons. In the figure, panel A shows an immunofluorescent-stained image with an anti-nestin antibody, panel B shows an immunofluorescent-stained image with an anti-TH antibody, and panel C shows a merged image of panel A and panel B. Scale bar represents 20 μm.
Figure 17:
Figure 17:

A medium was removed from a 60 mm dish containing the neural stem cells obtained in Example 4. Therefore, the cells were washed with Dulbecco's PBS (without Ca, Mg). Next, 2 ml of PBS was added to the above-mentioned 60 mm dish, and the cells were incubated at 37° C. for 5 minutes. Neural stem cells of which adhesion to a culture substratum was to be weakened were detached by pipetting, and centrifuged at 700×g for 5 minutes to harvest the neural stem cells. Next, 2 ml of the mixture of the astrocyte conditioned medium and the astrocyte basal medium was added to the above-mentioned neural stem cells to suspend the neural stem cells in the mixture. The suspension was plated on a 35 mm dish coated with a cell adhesion molecule. As a result, as shown in FIG. 17, it is found that the neural stem cells obtained in Example 4 are differentiated into neurons within several days even when the neural stem cells were once detached from the adhesive culture substratum to carry out the monolayer culture.

EXAMPLE 9

Differentiation of Cryopreserved Neural Stem Cells into Neurons

The neural stem cells were harvested in the same manner as in Example 8. The neural stem cells obtained were suspended in 10% (v/v) DMSO/90% (v/v) FCS, and cryopreserved at −80° C. in a deep freezer.

Figure 18:
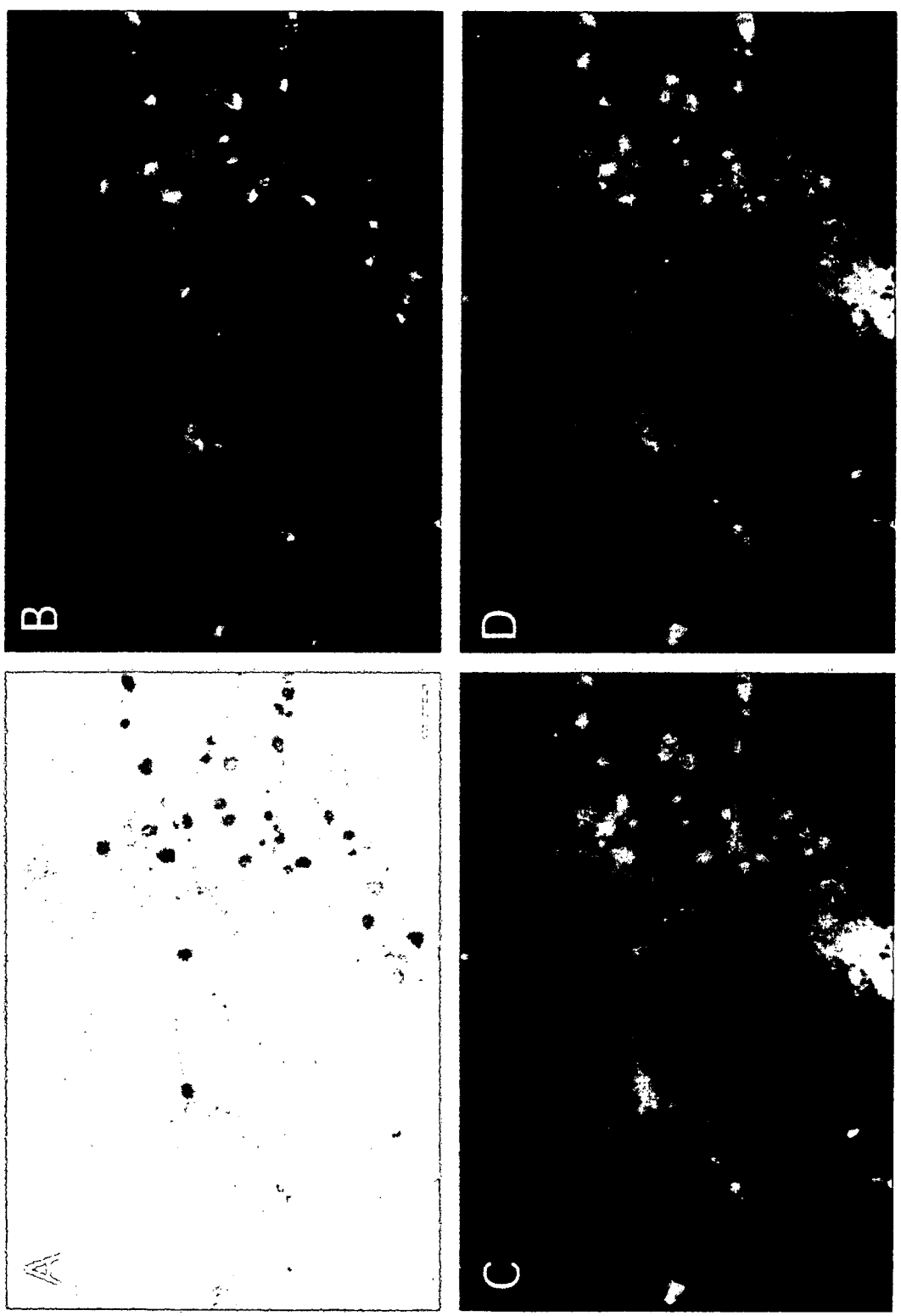
FIG. 18 is a photograph showing the results of examining the differentiation of cryopreserved neural stem cells into neurons. In the figure, panel A shows a phase contrast image, panel B shows an immunofluorescent-stained image with an anti-TH antibody, panel C shows an immunofluorescent-stained image with an anti-ChAT antibody, and panel D shows a merged image of panel A and panel B. Scale bar represents 20 μm.

The neural stem cells were washed to remove FCS by thawing the cryopreserved neural stem cells in an incubator at 37° C., adding 5 ml of DMEM to the product obtained, and centrifuging the mixture at 700×g for 5 minutes. Next, 2 ml of the mixture of the astrocyte conditioned medium and the astrocyte basal medium was added to the neural stem cells obtained to suspend the neural stem cells. Thereafter, the suspension was plated on a 35 mm dish coated with a cell adhesion molecule. FIG. 18 shows the results obtained by examining differentiation of cryopreserved neural stem cells into neurons.

As shown in FIG. 18, it is found that cryopreserved neural stem cells are differentiated into neurons in a period of several days, even when the monolayer culture of the cells was carried out. In other words, it is found that neural stem cells which can be prepared in a large amount can be used by freezing, and thawing where necessary.

EXAMPLE 10

Differentiation of Embryonic Stem Cell 129SV Cell Strain into Neurons

Figure 19:
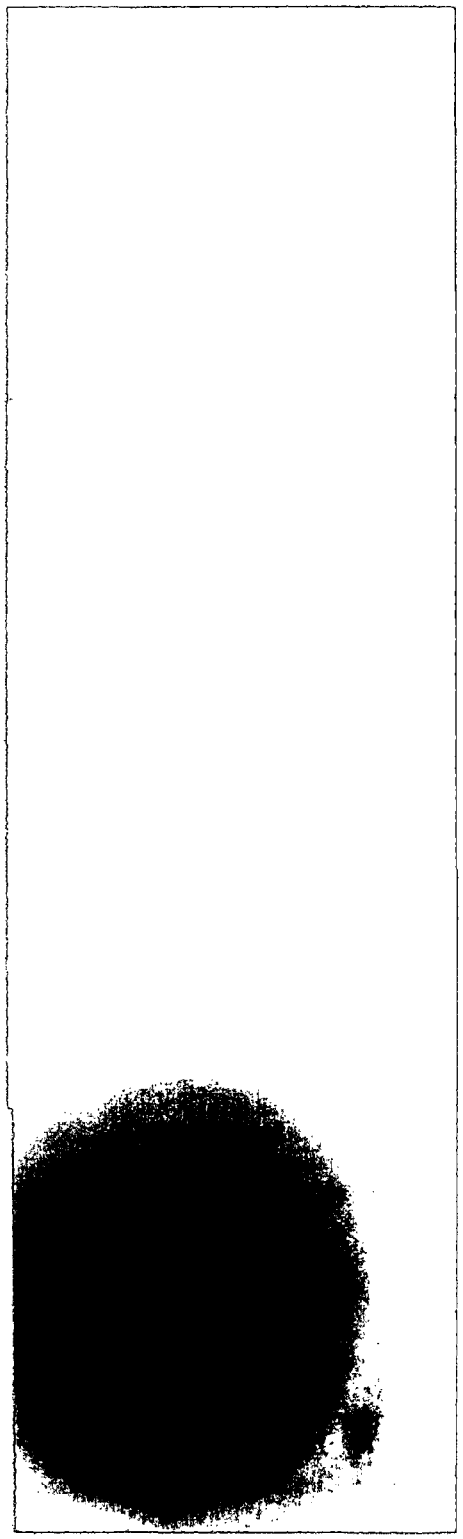
FIG. 19 is a photograph showing the results of carrying out the suspension culture of a commercially available embryonic stem cell established strain (129SV cell strain) in a mixture of an astrocyte conditioned medium and an astrocyte basal medium. Scale bar represents 50 μm.

The differentiation was studied under the same culture conditions as those of Examples 1 to 3 using commercially available 129SV mouse embryonic stem cells (passage number: 15, supplied by Dainippon Pharmaceutical Co., Ltd.) [Kontgen F. et al., *Int. Immunol.*, 5:957-964, (1993); Malissen M. et al., *EMBO J.*, 12: 4347-4355, (1993)] in place of the HK cell strain, embryonic stem cell prepared and established from C57BL/6 mouse blastocytes in Examples 1 to 3 mentioned above. FIG. 19 shows the results obtained by carrying out suspension culture in the mixture of the astrocyte conditioned medium and the astrocyte basal medium, and then carrying out the adhesion culture with the adhesive culture substratum.

As shown in FIG. 19, it is found that when the adhesion culture is carried out with the adhesive culture substratum after suspension culture, numerous neurites are elongated from the SCS obtained from the 129SV cell strains. In addition, by exchanging the medium during the adhesion culture with Neurobasal™ B-27 containing 20 ng/ml bFGF as a final concentration, the migration of the neural stem cells is caused, and the same phenomena as those of the HK cell strain are observed. In other words, it was clarified that a method comprising carrying out suspension culture of the embryonic stem cells in the mixture of the astrocyte conditioned medium and the astrocyte basal medium, thereby forming SCS, and thereafter carrying out adhesion culture can be applied even to embryonic stem cells from a different line of mouse.

In the case of the conditions other than the suspension culture, since not only neural cells but also other cells may be confirmed in some cases, selective differentiation into neural cells has been difficult.

EXAMPLE 11

Differentiation of Cynomolgus Monkey Embryonic Stem Cell (CMK-6) into Neuron

Whether or not the embryonic stem cell strain established from cynomolgus monkey, CMK-6 cell strain [Suemeri, H. et al., *Dev. Dyn.*, 222:273-279, (2001)] was differentiated into neurons was studied by carrying out suspension culture in the mixture of the astrocyte conditioned medium and the astrocyte basal medium, and carrying out adhesion culture with an adhesive culture substratum in the same manner as in the mouse embryonic stem cells.

The CMK-6 cell strain was cultured in DMEM: F-12 (1:1) containing as final concentrations 13.3% (w/v) FCS and $10^3$ U/ml LIF, using mouse primary fibroblasts as a feeder cell layer. The culture conditions were 37° C. and 5% $CO_2$.

At a stage where the colony of CMK-6 cell strain was grown to a size of from 400 to 500 μm, the colony was mechanically detached from a feeder cell layer with a glass capillary in the same manner as those of the mouse. Next, the suspension culture of 10 to 20 colonies of the CMK-6 cell strain obtained was carried out in 2 ml of the mixture of the astrocyte conditioned medium and the astrocyte basal medium in the 35 mm bacterial dish in an atmosphere of around 37° C., a $CO_2$ concentration of about 5% and 100% humidity.

While the mouse embryonic stem cells form a colony in the swelled state, since the colony of the CMK-6 cell strain was flat, the colony immediately after detaching was suspended in a state similar to that where the paper was twisted. However, after several hours, the CMK-6 cell strain formed a spherical form by intracellular adhesion of the embryonic stem cells to each other.

In addition, since the CMK-6 cell strain was proliferated slower than the mouse embryonic stem cells, it took more time to increase the size of the SCS from the CMK-6 cell strain even in the suspension culture.

In order to examine the state of differentiation into neural stem cells upon the formation of the SCS of cynomolgus monkey embryonic stem cells (CMK-6 cell strain), the suspension culture of the cells was carried out for 10 to 12 days in the mixture of the astrocyte conditioned medium and the astrocyte basal medium, and thereafter fixed. The distribution for primates was examined with an anti-nestin antibody from a rabbit in the same manner as the case from the mouse. Further, the SCS after the suspension culture was adhered to an adhesive substratum, and the reactivity to nestin for the cells which were allowed to migrate after 7 to 10 days was also examined. The results are shown in FIG. 20.

Figure 20:
FIG. 20 is a photograph showing the distribution of nestin when SCS was prepared in CMK-6 cell line of an embryonic stem cell strain established from a cynomolgus monkey. In the figure, panel A is an immunofluorescent-stained image of suspended SCS with an anti-nestin antibody. In the figure, panel B is an immunofluorescent-stained image of cells in which SCS is adhered and allowed to migrate, with an anti-nestin antibody. Scale bar represents 50 μm.
Figure 20:
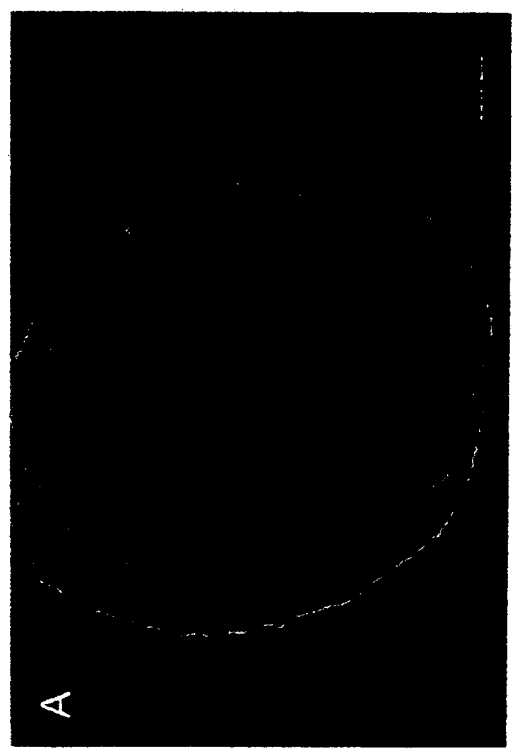

As shown in FIG. 20, since the whole suspended SCS is stained with the anti-nestin antibody, and the cells migrated from the adhered SCS are also stained with the anti-nestin antibody, it was shown that the neural stem cells can be prepared by carrying out suspension culture of the neural stem cells in the mixture of the astrocyte conditioned medium and the astrocyte basal medium as efficiently as in the case of the mouse.

Figure 21:
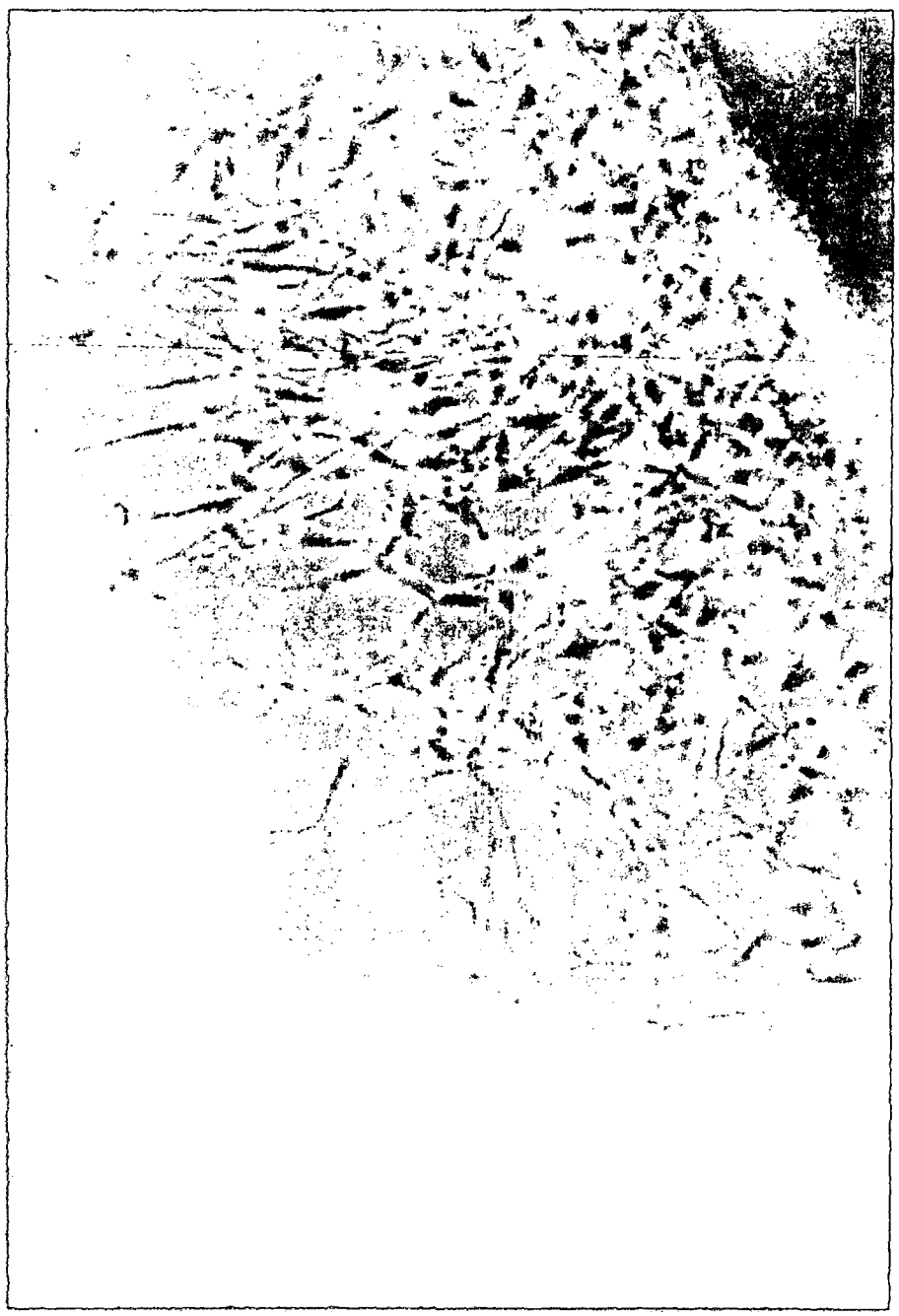
FIG. 21 is a photograph showing the results of carrying out the suspension culture of CMK-6 cell line from a cynomolgus monkey in a mixture of an astrocyte conditioned medium and an astrocyte basal medium. Scale bar represents 20 μm.

The results obtained by observation of SCS and its surroundings with a phase contrast microscope on the day 1 of the adhesion culture are shown in FIG. 21.

As shown in FIG. 21, it is found that in the same manner as in the SCS from the mouse embryonic stem cells, neurons are migrated from the SCS from the cynomolgus monkey embryonic stem cells on the day 1 after the adhesion culture, elongating the neurites. In addition, as observed also in the adhered SCS from the mouse embryonic stem cells, it is found that the cells are differentiated into neurons in the SCS, and actively elongated their neurites from the SCS.

In addition, the expression of a synthase of a neurotransmitter in neurons migrating from the SCS obtained from the cynomolgus monkey embryonic stem cell CMK-6 cell strain was examined by an immunohistochemical technique in the same manner as the detection of nestin in Example 1 mentioned above. The results are shown in FIG. 22.

Figure 22:
FIG. 22 is a photograph showing the results of examining expression of a neurotransmitter synthase in neurons which are migrated from SCS obtained from CMK 6 cell line of embryonic stem cells of a cynomolgus monkey. In the figure, panel A shows an immunofluorescent-stained image with an anti-TH antibody, panel B shows an immunofluorescent-stained image with an anti-NF antibody, and panel C shows a merged image of panel A and panel B. Scale bar represents 20 μm.
Figure 22:
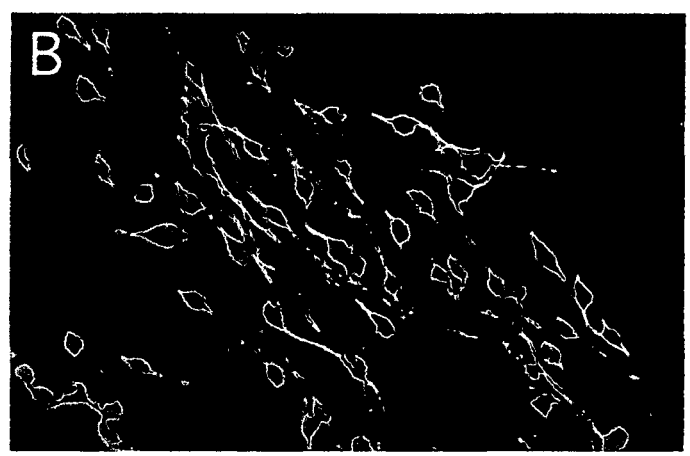
Figure 22:
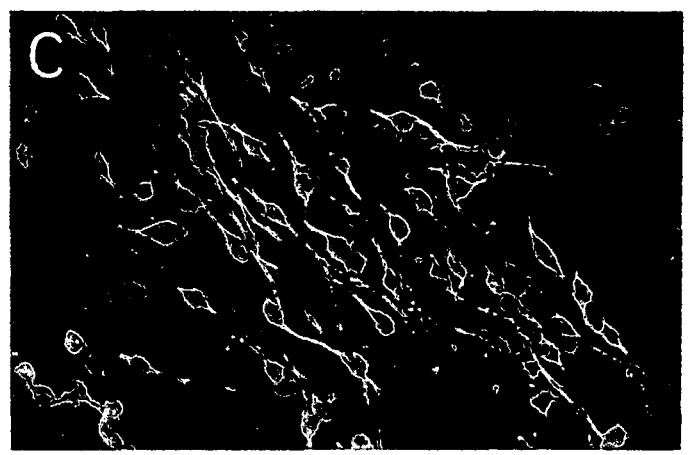

As shown in FIG. 22, since the majority of NF-positive neurons are TH-positive, it is found that dopaminergic neurons were differentiated. In other words, it is found that the cynomolgus monkey embryonic stem cell CMK-6 cell strain is easily differentiated into neurons by carrying out suspension culture of the cell strain in the mixture of the astrocyte conditioned medium and the astrocyte basal medium, and carrying out adhesion culture using an adhesive culture substratum.

It is found that from this finding that the method comprising carrying out suspension culture in the mixture of the astrocyte conditioned medium and the astrocyte basal medium, and carrying out adhesion culture, to differentiate cells into neurons can be also universally applied to embryonic stem cells of a cynomolgus monkey a primate, which is a species different from a mouse. In addition, it is thought that the above method is effective beyond species, and has universality. Further, in consideration of the fact that a cynomolgus monkey is a primate, there is a possibility that this method can be also applied to human embryonic stem cells.

In the case of conditions other than the suspension culture, not only neural cells but also other cells may be found in some cases, so that the selective differentiation into neural cells becomes difficult.

EXAMPLE 12

Analysis of Gene Expression

Mouse-Derived HK Strain

The gene expression accompanied with the differentiation from undifferentiated embryonic stem cells into neurons was examined.

Suspension culture of the undifferentiated embryonic stem cells was carried out for 4 days in an atmosphere of 37° C., 5% $CO_2$ in the air and 100% humidity, thereby forming SCS. Next, the adhesion culture of the SCS was carried out for 5 days in an atmosphere of 37° C., 5% $CO_2$ in the air and 100% humidity to induce the differentiation into neurons.

mRNA was prepared by a conventional method from 20 each of the undifferentiated embryonic stem cells, the SCS formed by carrying out the suspension culture, and the cell masses obtained by carrying out the adhesion culture. cDNA was synthesized by carrying out a reverse transcription reaction at 37° C. for 60 minutes using a random hexamer as a primer with mRNA obtained as a template.

As the primer, a primer for amplifying each of Oct-4 (transcription regulatory factor peculiar to ES cell), Pax-6 (transcription regulatory factor peculiar to neuronal precursor), nestin, NF-M, Nurr1 (dopamine neuron marker), TH, GATA4 (endoderm marker), Brachyury (mesoderm marker), cytokeratin 17 (ectoderm epidermal cell marker), β-actin and GAPDH was used.

Next, PCR was carried out using the above-mentioned primers for each of Oct-4 (24 cycles) Pax-6 (30 cycles), nestin (26 cycles), NF-M (30 cycles), Nurr1 (26 cycles), TH (30 cycles), GATA4 (30 cycles), Brachyury (30 cycles) and β-actin (22 cycles) with cDNA as a template in an amount so that an amount of the PCR product of a fragment corresponding to GAPDH is equal among the undifferentiated embryonic stem cells, the SCS formed by carrying out the suspension culture, and the cell masses obtained by carrying out the adhesion culture. The thermal profile of PCR was so that one cycle of reaction consisting of 95° C. for 15 seconds, 58° C. for 30 seconds, and 72° C. for 45 seconds. Each of the products obtained was subjected to electrophoresis and analyzed. The results are shown in FIG. 23.

Figure 23:
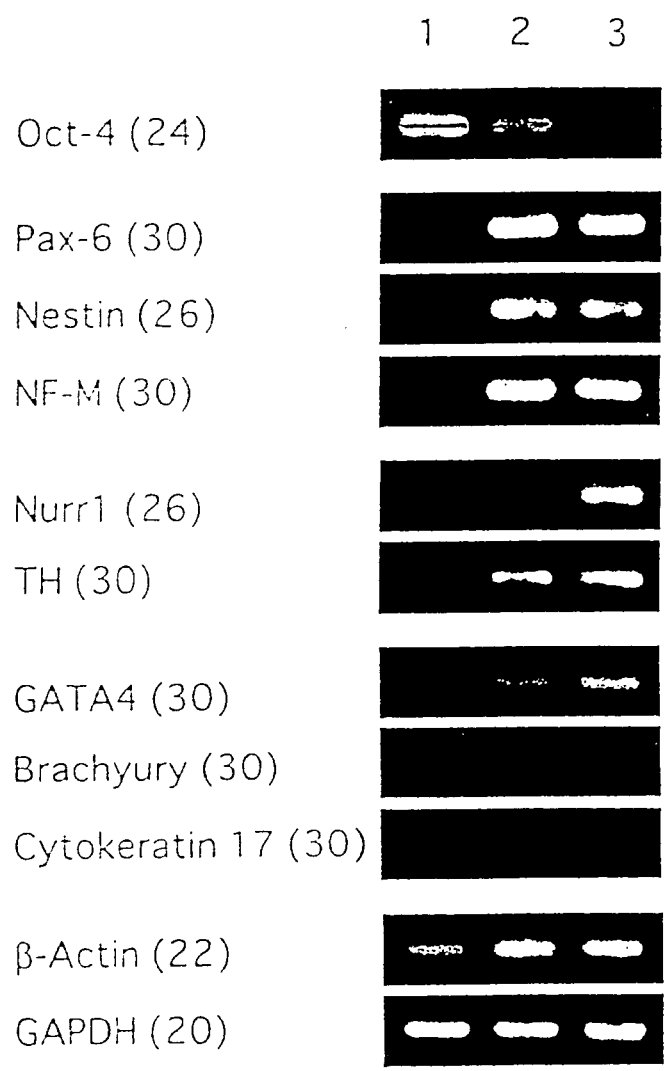
FIG. 23 is a photograph showing the results of examining gene expression accompanied with differentiation from embryonic stem cells into neurons. In the figure, lane 1 shows an undifferentiated embryonic stem cell clone, lane 2 shows SCS formed by carrying out suspension culture for 4 days, and lane 3 shows the results of a cell mass obtained by carrying out culture in the state of adhesion for 5 days.

As shown in FIG. 23, it is found that Oct-4 detected in the embryonic stem cells (lane 1) is decreased in the suspended SCS (lane 2), and that a very weak signal is found in the state of differentiation into nerves in the adhered SCS (lane 3). In addition, it is found that expression of nestin, which is expressed in the neural stem cells, is rapidly increased in the suspended SCS and expression continues also in the stage of the adhered SCS. The expression profile of nestin is well consistent with a rapid division of the neural stem cells and differentiation thereof into neurons. Further, it is found that gene expression is enhanced in NF, which is expressed only in neurons, TH, which is a synthase for dopamine neurons and Nurr1, which is its transcription factor, as each is differentiated from the suspended SCS into the adhered SCS. In addition, since there are hardly any changes in expression of a marker gene for an endoderm, a mesoderm and an ectoderm in the differentiated neurons obtained by the method comprising carrying out the suspension culture of the embryonic stem cells in the mixture of the astrocyte conditioned medium and the astrocyte basal medium, thereby forming SCS, and thereafter carrying out the adhesion culture. Therefore, it is clear that the above-mentioned method is different from the method of differentiation by forming EB.

Next, a quantitative change with the passage of time was examined. Suspension culture of an undifferentiated embryonic stem cell clone was carried out for 4 days in the mixture of the astrocyte conditioned medium and the astrocyte basal medium, thereby forming SCS, and thereafter the adhesion culture of the SCS was carried out for 5 days to induce the differentiation of the SCS into neurons. mRNA was prepared by a conventional method from 4 or 5 each of the undifferentiated embryonic stem cell clone (suspension culture: the day 0), the SCS on the day 2 and the day 4 of the suspension culture, and the cell masses of the day 2 and the day 5 of the adhesion culture. cDNA was synthesized by carrying out a reverse transcription reaction with mRNA obtained as a template.

Subsequently, in order to analyze the amount of mRNA for GAPDH, Oct-4, nestin and TH, PCR having the same cycle numbers as those described above was carried out to quantify the amount of the product, whereby the amounts of mRNA of GAPDH, Oct-4, nestin and TH in the sample were determined semi-quantitatively. Thereafter, each of the amounts of Oct-4, nestin and TH was divided by the amount of GAPDH to obtain a relative expression level as Oct-4/GAPDH, nestin/

GAPDH and TH/GAPDH, and further shown in the graph by defining a maximum of a relative expression level as 1. The results are shown in FIG. 24.

Figure 24:
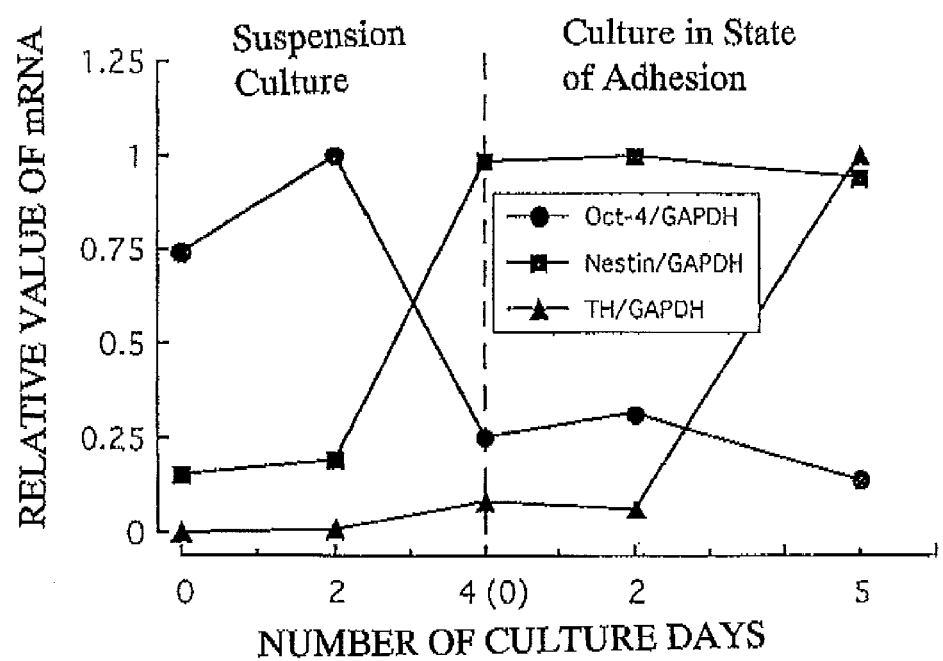
FIG. 24 is a view showing a change in gene expression with the passage of time, accompanied with differentiation from embryonic stem cells into neurons. Each of the levels of Oct-4, nestin (in the figure, Nestin) and TH is divided by the level of GAPDH, to give a relative expression level of Oct-4/GAPDH, nestin/GAPDH or TH/GAPDH, and shown in the graph, wherein a maximum of the relative expression level is defined as 1.

As a result, as shown in FIG. 24, it is found that in nestin, which is expressed in the neural stem cells, the expression is rapidly enhanced in the suspended SCS, and that the expression continues even at a stage of the adhered SCS. The expression profile of nestin is well consistent with rapid division of neural stem cells and differentiation thereof into neurons. Further, it is found that gene expression is enhanced as TH, which is a synthase of dopamine neurons, is differentiated from the suspended SCS into the adhered SCS.

INDUSTRIAL APPLICABILITY

According to the method for producing a substantially isolated neural cell of the present invention, a substantially isolated neural cell can be efficiently supplied in a large amount and stably from embryonic stem cells without being limited in a source of the embryonic stem cells and without inducing an ectodermal cell, a mesodermal cell and an endodermal cell other than the neural cell, so that the neural cell suitable for transplantation can be supplied in a large amount and stably. Therefore, an application to neuroregenerative therapy or the like is expected. In addition, since the neural cell of the present invention is selectively differentiated via the embryonic stem cells into any one of neurons and glial cells from neural stem cells, the neural cell can be used as a source of a cell or a tissue in neuroregenerative therapy or the like for neuroregenerative disease, spinal damage, cerebral infarct or the like. Further, the neuron of the present invention enables release of a neurotransmitter and reconstruction of communication between nerve in regeneration of medical treatment such as neuronal transplantation therapy for neurodegenerative disease, spinal damage, cerebral infarct or the like. Further, according to the glial cell of the present invention, simultaneous transplantation of the glial cell with a neuron and a neural stem cell enables to support the differentiation and growth of a neuron, and further to form a brain-blood barrier for supplement of a nutrient substance.

The invention claimed is:

1. A method for producing isolated neural stem cells, wherein the method comprises:
    (A) culturing undifferentiated primate embryonic stem cells in suspension in the presence of an astrocyte conditioned medium thereby forming a stem cell sphere (SCS) comprising a neural stem cell layer, a pre-neural stem cell layer, and an embryonic stem cell layer and
    (B) adhering the stem cell sphere (SCS) obtained in step (A) to an adhesive culture substratum carrying a cell adhesion molecule and culturing the stem cell sphere (SCS) in the presence of basic fibroblast growth factor (bFGF) and/or epidermal growth factor (EGF), and
    (C) obtaining neural stem cells as they migrate from the SCS.

2. The method for producing neural cells according to claim 1, further comprising:
    (D) culturing the SCS by adhering the SCS to an adhesive culture substratum comprising a cell adhesion molecule and in the absence of bFGF and/or EGF, and
    (E) obtaining glial cells as they migrate from the SCS.

3. The method according to claim 1, wherein the astrocyte conditioned medium comprises an astrocyte basal medium and a supernatant from an astrocyte cell culture.

4. The method according to claim 1, wherein the astrocyte conditioned medium is conditioned by astrocytes obtained by culture from the membrane cerebra from the brain of a primate.

5. A method for producing isolated neural cells, wherein the method comprises:
    (A) culturing undifferentiated primate embryonic stem (ES) cells in suspension in a mixture of astrocyte conditioned medium and astrocyte basal medium, wherein stem cell spheres (SCS) are formed comprising: nestin-positive/BrdU-negative neural stem cells on the surface layer; pre-neural stem cell layer negative for both nestin and BrdU on the mantle layer and nestin negative/BrdU-positive ES cells on the core layer, and subsequently;
    (B) culturing the stem cell spheres (SCS) in suspension obtained in step (A) in the presence of basic fibroblast growth factor (bFGF) and/or epidermal growth factor (EGF) and in the presence of a cell adhesion molecule, and
    (C) obtaining neural stem cells.

6. The method for producing neural cells according to claim 5, further comprising:
    (D) culturing the SCS by adhering the SCS to an adhesive culture substratum comprising a cell adhesion molecule and in the absence of bFGF and/or EGF, and
    (E) obtaining glial cells as they migrate from the SCS.

7. The method according to claim 5, wherein the astrocyte conditioned medium comprises an astrocyte basal medium and a supernatant from an astrocyte cell culture.

8. The method according to claim 5, wherein the astrocyte conditioned medium is conditioned by astrocytes obtained by culture from the membrane cerebra from the brain of a primate.

* * * * *